US011572573B2

(12) United States Patent
Lai et al.

(10) Patent No.: US 11,572,573 B2
(45) Date of Patent: Feb. 7, 2023

(54) METHOD FOR PROPAGATING STERILE MALE PLANT LINE

(71) Applicant: China Agricultural University, Beijing (CN)

(72) Inventors: Jinsheng Lai, Beijing (CN); Haiming Zhao, Beijing (CN); Weibin Song, Beijing (CN); Yang Cui, Beijing (CN)

(73) Assignee: China Agricultural University, Bejing (CN)

( * ) Notice: Subject to any disclaimer, the term of this patent is extended or adjusted under 35 U.S.C. 154(b) by 0 days.

(21) Appl. No.: 16/370,628

(22) Filed: Mar. 29, 2019

(65) Prior Publication Data

US 2019/0218572 A1 Jul. 18, 2019

Related U.S. Application Data

(62) Division of application No. 14/437,633, filed as application No. PCT/CN2013/001269 on Oct. 18, 2013, now Pat. No. 10,246,723.

(30) Foreign Application Priority Data

Oct. 23, 2012 (CN) ........................ 201210406154.1
Oct. 23, 2012 (CN) ........................ 201210406155.6

(51) Int. Cl.

| | |
|---|---|
| ***C12N 15/82*** | (2006.01) |
| ***A01H 1/00*** | (2006.01) |
| ***A01H 5/10*** | (2018.01) |
| ***C12N 15/00*** | (2006.01) |
| ***A01H 1/02*** | (2006.01) |
| ***A01H 6/46*** | (2018.01) |

(52) U.S. Cl.

CPC .......... *C12N 15/8289* (2013.01); *A01H 1/00* (2013.01); *A01H 1/02* (2013.01); *A01H 6/4684* (2018.05); *C12N 15/00* (2013.01); *C12N 15/821* (2013.01); *C12N 15/8218* (2013.01); *C12N 15/8287* (2013.01)

(58) Field of Classification Search

None

See application file for complete search history.

(56) References Cited

U.S. PATENT DOCUMENTS 5,880,331 A 3/1999 Krebbers et al.
2008/0244765 A1 10/2008 Zhao et al.
2009/0038028 A1* 2/2009 Albertsen ............ C07K 14/415 800/274
2010/0064385 A1* 3/2010 He ...................... C07K 14/415 800/278
2011/0173725 A1 7/2011 Wu et al.

FOREIGN PATENT DOCUMENTS

| | | |
|---|---|---|
| CN | 1156951 A | 8/1997 |
| CN | 1913772 A | 2/2007 |
| CN | 102960234 A | 3/2013 |
| CN | 102965391 A | 3/2013 |

OTHER PUBLICATIONS

Cigan, A.M., et al., "Phenotypic complementation of ms45 maize requires tapetal expression of MS45," Sex Plant Reprod (2001) 14:135-142.

Fox, T.W. et al., Genbank Accession No. AF 360356.1 [Zeamaysmalefertilityprotein (Ms45)] May 12, 2001, from GenBank database.

Kim, C. S. et al., "The maize Mucronate mutation is a deletion in the 16-kDa γ-zein gene that induces the unfolded protein response," The Plant Journal (2006) 48, 440-45.

Michael E. Miller and Prem s. Chourey, "The Maize Invertase-Deficient miniature-1 Seed Mutation is Associated with Aberrant Pedicel and Endosperm Development," The Plant Cell, vol. 4, 297-305, Mar. 1992.

International Search Report dated Jan. 30, 2014 for PCT/CN2013/001269.

* cited by examiner

*Primary Examiner* — Phuong T Bui

(74) *Attorney, Agent, or Firm* — Knobbe, Martens, Olson & Bear, LLP

(57) ABSTRACT

A method for maintaining a male sterile plant in a homozygous recessive state includes providing a first plant that includes homozygous recessive male sterility alleles, providing a second plant that includes homozygous recessive male sterility alleles the same as that in the first plant and a nucleotide construct in which the construct exists in a heterozygous state. The first nucleotide sequence of the nucleotide construct encodes a first protein that restores male fertility of the first plant after expression in the first plant. The second nucleotide sequence of the nucleotide construct allows for distinguishing the grains with or without the construct by observation through naked eyes or devices. The first nucleotide sequence and the second nucleotide sequence are tightly connected with each other and coexist in a plant. The method further includes fertilizing female gametes of the first plant with male gametes of the second plant.

5 Claims, 7 Drawing Sheets

Specification includes a Sequence Listing.

SEQUENCE LISTING

```
<160> NUMBER OF SEQ ID NOS: 12

<210> SEQ ID NO 1
<211> LENGTH: 3518
<212> TYPE: DNA
<213> ORGANISM: Artificial sequence
<220> FEATURE:
<223> OTHER INFORMATION: Synthetic sequence

<400> SEQUENCE: 1

tgaattctgc tgagttctcc ttgggttatc catggtgtct ctatgaaaaa gatgagtaca      60

atgtgtctat atccgttttc ttagggtccc ttcttctgcc ttattactga ctgaatcggg     120

gttacaaaaa aacttccacg ggtgcatgat ctccatgttc cacttctccc acctcgcgtt     180

gcacatttct tggatgtcgg tggttcccat ctgaccgagg cccatcagac acctttcggg     240

acacccatca agggcctttc ggatggccca cgagacgtat cgggtcgtgg tgatccaggg     300

gatatatgtc ccccacaatc gtcacctata ttattattct ttagatatta tttaattttt     360

ggaaaaataa caaacttata cttttgtgta gggcctcagc atagattttc gcttagggcc     420

cagaaatgcg aggaccagcc atgtctagtg tccactattg gcactaccca gaacaagatt     480

taaaaaaata accaaagtaa ctaatccact cgaaagctat catgtaatgt ttaaagaaac     540

atctattaaa accacgatcc tcttaaaaaa caagcatatt tcgaaagaga caaattatgt     600

tacagtttac aaacatctaa gagcgacaaa ttatatcgaa aggtaagcta tgacgttcag     660

atttttcttt ttcattcttg ttattttgtt attgttttta tatacatttt cttctcttac     720

aatagagtga ttttcttccg attttataaa atgactataa agtcattttt atataagagc     780

acgcatgtcg tagattctcg ttcaaaaatc tttctgattt ttttaagagc tagtttggca     840

accctgtttc tttcaaagaa ttttgatttt ttcaaaaaaa attagtttat tttctcttta     900

taaaatagaa aacacttaga aaaatagagt tgccagacta gccctagaat gttttcccaa     960

taaattacaa tcactgtgta taattatttg gccagcccca taaattattt aaaccgaaac    1020

tgaaatcgag cgaaaccaaa tctgagctat ttctctagat tagtaaaaag ggagagagag    1080
```

-continued

```
aggaagaaat cagttttaag tcattgtccc tgagatgtgc ggtttggcaa cgatagccac   1140
cgtaatcata gctcataggt gcctacgtca ggttcggcag ctctcgtgtc atctcacatg   1200
gcatactaca tgcttgttca accgttcgtc ttgttccatc gtccaagcct tgcctattct   1260
gaaccaagag gatacctact cccaaacaat ccatcttact catgcaactt ccatgcaaac   1320
acgcacatat gtttcctgaa ccaatccatt aaagatcaca acagctagcg ttctcccgct   1380
agcttccctc tctcctctgc cgatcttttt cgtccaccag catggagaag aggaacctgc   1440
agtggcggcg agggcgtgat ggcatcgtgc agtaccctca cctcttcttc gcggccctgg   1500
cgctggccct cctagtcgcg gacccgttcg gcctcagtcc gctggccgag gtcgactacc   1560
ggccggtgaa gcacgagctc gcgccgtacg gggaggtcat gggcagctgg cccagagaca   1620
atgccagccg gctcaggcgc gggaggctgg agttcgtcgg cgaggtgttc gggccggagt   1680
ctatcgagtt cgatctccag ggccgcgggc cgtacgccgg cctcgccgac ggccgcgtcg   1740
tgcggtggat gggcgaggag gccgggtggg agacgttcgc cgtcatgaat cctgactggt   1800
aagtgctcga tatcgctccg gcgtccactc gttacatgct ataatatagt agtactaaga   1860
tattttgatc tgattttttg cattcttggg agaaacgtca tgcaaaattt gttgtttctt   1920
ggcaaaggtc agaagaagtc tgtgccaatg gagtgaactc aacgacgagg aagcagcacg   1980
agaaggagga gttctgcggc cggccgctcg gcctgaggtt ccacggggag accggcgagc   2040
tctacgtcgc cgacgcgtac tacggtctca tggtcgttgg ccagagcggc ggcgtggcgt   2100
cctccgtcgc gagggaagcc gacggggacc ccatccggtt cgcgaacgac ctcgatgtgc   2160
acaggaatgg atccgtattc ttcactgaca cgagcatgag atacagcaga aagtgagcaa   2220
agcgacgtaa caatccggct tctcattttc aaacgcctct gtattctctg ctgaaagagt   2280
agctcaccag acaagagctg aatttgcagg gaccatctga acatcctgtt agaaggagaa   2340
ggcaccggga ggctgctcag gtatgatcca gaaacaagcg gtgtccatgt cgtgctcaag   2400
gggctggtgt tcccaaacgg cgtgcagatc tcagaggacc atcagtttct tctcttctcc   2460
gagacaacaa actgcaggta acaaaaatac tatctgacga tgctcatgat tctaccgtat   2520
ccatagtcat gaacacaaac cacacgaatc tggccttgac caggataatg aggtactggc   2580
tggaaggccc aagagcgggc gaggtagagg tgttcgcgaa cctgccgggc ttccccgaca   2640
acgtgcgctc caacggcagg ggccagttct gggtggcgat cgactgctgc cggacgccgg   2700
cgcaggaggt gttcgccaag aggccgtggc tccggaccct gtacttcaag ttcccgctgt   2760
cgctcaaggt gctcacttgg aaggccgcca ggaggatgca cacggtgctc gcgctcctcg   2820
acggcgaagg gcgcgtcgtg gaggtgctcg aggaccgggg ccacgaggtg atgaagctgg   2880
tgagcgaggt gcgggaggtg ggccgcaagc tgtggatcgg aaccgtggcg cacaaccaca   2940
tcgccaccat cccctaccct ttagaggact aaccatgatc tatgctgttt caatgcctcc   3000
taatctgtgt acgtctataa atgtctaatg cagtcactgg ttgtaatctt gtttgtgttt   3060
ggcaaattgg cataataatg gacagattca atgggcattg gtgctgtagt cgcatcacac   3120
taattgaatg ggatcatgtt gagctctcac tttgctacaa tttgctccag cttgtacggt   3180
tgtaccctct tgctcgtcta tagtaagggc catctaaaaa aaactcaaat tagatctgca   3240
atacaagtat gattgggccg aatttggatt gtcacgggtc cgcgaccgcg aattgggctc   3300
ggtttgattt agccgacata gtagtgaccg acccgagccg gcggcgagcc aaaccgagcg   3360
gacgccgcca tggatcgcga gtggggctcc aagcccggca gcggcggcgc cgcctccgcg   3420
```

-continued

```
cagaatgagg ccatcgaccg gcgggagcgc ctccgccgcc tggccctcga gaccatcgac   3480

ctcgccaagg acccctattt catgcgcaac ccccggga                           3518


<210> SEQ ID NO 2
<211> LENGTH: 675
<212> TYPE: DNA
<213> ORGANISM: Artificial sequence
<220> FEATURE:
<223> OTHER INFORMATION: Synthetic sequence

<400> SEQUENCE: 2

ggatccggtg acctaagttt cgcttcggcg tgcttgctgc tgctgttgca gctcgcagga     60

gcgtcgcatg tcgtctacaa ctacaaggac ctcgaagccg aggctgctgc ggcgacggac    120

caggtgccgc cgtccatcgt caaccccctg ctcaggacgg ggtaccactt ccagcccccc    180

aagaactgga tcaatgcgcc catgtactac aaggggtggt accatttctt ctaccaatac    240

aatcccaagg gcgccgtatg ggcaacatc gtgtggacta gtagagggta attaagcaaa     300

acttatccaa aactaaacat tttactatta ttttgacctt tttattccac ttttcttaga    360

caatgattta acctcgtaat caattgttag gatttctagt ccacacgatg ttgccccata    420

cggcgccctt gggattgtat tggtagaaga aatggtacca ccccttgtag tacatgggcg    480

cattgatcca gttcttgggg ggctggaagt ggtaccccgt cctgagcagg gggttgacga    540

tggacggcgg cacctggtcc gtcgccgcag cagcctcggc ttcgaggtcc ttgtagttgt    600

agacgacatg cgacgctcct gcgagctgca acagcagcag caagcacgcc gaagcgaaac    660

ttaaagcttg gatct                                                     675


<210> SEQ ID NO 3
<211> LENGTH: 2442
<212> TYPE: DNA
<213> ORGANISM: Zea mays

<400> SEQUENCE: 3

gccagctcgc atgagagaac aaccagacca gccgaagcat tacgcgaggc attaagacct     60

caaaggagtg aaaccactcc tccgaggcct cgggggctac acccggcggg tgcgctcgcg    120

cgcacccacc ggaacaaaat gcaaccgaga aaggctggtc cccttgcaaa aaagtgcgac    180

gaaagcctcc aagcgagtgc taacactccc ttcgaggctc gggggctact gtcggggacc    240

ataattaggg gtaccctcaa gactcctaat tctcagctgg taaccccccat cagcataaag   300

ctgctaaggc ctgatgggtg cgattaagtc agggattagt ccgttcgagc gactcgatca    360

cgcctcgccc gagcctagcc tcggacaagg gcagccgacc ccgaaggatt tccgtctcgc    420

ccgaggcccc cctccaacgg cgaacatatt tccggctcgc ccgagccctg ccttcgctaa    480

gaagcaaccc tgactaaatc accgcaccga ccgaccaaat cgcaggagca tttaatgcaa    540

aggtggcctg acacctttat cctgacgcgc gccccccggc agagccgaag tgaccgccgt    600

cacttcgccg ctccactgac cggcctgaca gaaggacagc gtcgcctgcg ccactctgac    660

tgcagtgcca cttgacagag tgagactgac aggcagtcag gccctgccga aggcaccata    720

ggaagctccg cttcgcccga cccagggctc ggactcgggc taagtcccgg aagacggcga    780

actccgctcc gcccgaccca gggctcggac tcgggctaag tcccggaaga cggcgaactc    840

cgctccgccc gacccagggc tcggactcgg gctaagtccc ggaagacggc gaactccgct    900

ccgcccgacc cagggctcgg actcgggctc agccccagaa gacgacgaac tccgcttcgc    960

ccgacccagg gctcggactc cgccctggcc tcagccgacg gcctccgcct cgcccgaccc   1020
```

-continued

```
aggggctcgg actcggcctc ggccacggaa gacagactcg acctcggctt cggaggagcc   1080

tccacatcgc ccaacctagg gcgcaggcca gccacgtcaa caggaggcgc catcatcacc   1140

ctaccccgag ctgactcggg ccgcagggaa caagaccggc gtcccatctg gctagctccg   1200

ccagataggc aatgatggcg ccccgcatac tctgtaacga cggcggctct cagcccccctt  1260

acggaagcaa gaggacgtca gcaaggaccc aaccgctccg acagctgtcc ctccgccagg   1320

ctccatcgct cctccgacgg ccacgacatc acaccagctg ggtgccaaag tctctccgtc   1380

tgccacaacg gcatgtactt agggcgctag ctctcctccg ctagacacgt agcactctgc   1440

tacacccccc attgtacacc tggatcctct ccttacgcct ataaaaggaa ggaccagggc   1500

cctcttggag agggttggcc gcgcggggac gaggacgaga caggcgctcg cctggagccg   1560

ctcgctccct ctcccgcgtg gacgcttgta accccctact gcaagcgcac ccgaccgggg   1620

cgcgggacga acatgaaggc cgcgggattc ccacctctct cacgccggtc tccggccgcc   1680

tcgctctccc cccttcgcgc tcgccctcgc gctcgaccca tctgggctgg ggcacgcggc   1740

gacactcact cgtcggccca gggacccccc ggtctcgaaa cgtcgacaca tttaatgctt   1800

aatctaacaa taattacttt tatatatttg atcgaacttt aaaagatttg gctcctcaga   1860

aagatagacg atgtgcattt attttagaaa tgataggata tatttaaggc gacatatgga   1920

atagacaggt tgggatggag tagatatata tagattcata cgactaaagt tgtgttcagc   1980

agatcatata tatagctatg caaaacacta ttttacactg tagatagcaa tatttatgtt   2040

gtttagagag tgaattttga aataagaggt gagatagaga atgtgatatg gcagctaaga   2100

gctagttttc aacaagtttg tttctataat agtatagcta gatagacaga cacgtagcta   2160

aaatggtcaa ctgaccttcg tacaaaaaaa aactttaatc cagagatata gcaatatatg   2220

cttataactc cagacctcag agtcaaccca cagatttttg tatattcgtc aaaaagatcc   2280

acagatttgt ggtagagagt atgttttagt agtagtggta tatctccctt gtgggacgac   2340

gaagcagccg gtcagccggc gctccggccg gccggccggc ctgcgcctgc acagtacaaa   2400

tagcaccccc cgtcctccag ttggctgcat ccttctagct tc                      2442
```

<210> SEQ ID NO 4
<211> LENGTH: 412
<212> TYPE: PRT
<213> ORGANISM: Zea mays

<400> SEQUENCE: 4

```
Met Glu Lys Arg Asn Leu Gln Trp Arg Arg Gly Arg Asp Gly Ile Val
1               5                   10                  15

Gln Tyr Pro His Leu Phe Phe Ala Ala Leu Ala Leu Ala Leu Leu Val
            20                  25                  30

Ala Asp Pro Phe Gly Leu Ser Pro Leu Ala Glu Val Asp Tyr Arg Pro
        35                  40                  45

Val Lys His Glu Leu Ala Pro Tyr Gly Glu Val Met Gly Ser Trp Pro
    50                  55                  60

Arg Asp Asn Ala Ser Arg Leu Arg Arg Gly Arg Leu Glu Phe Val Gly
65                  70                  75                  80

Glu Val Phe Gly Pro Glu Ser Ile Glu Phe Asp Leu Gln Gly Arg Gly
                85                  90                  95

Pro Tyr Ala Gly Leu Ala Asp Gly Arg Val Val Arg Trp Met Gly Glu
            100                 105                 110

Glu Ala Gly Trp Glu Thr Phe Ala Val Met Asn Pro Asp Trp Ser Glu
```

```
        115                 120                 125

Glu Val Cys Ala Asn Gly Val Asn Ser Thr Thr Arg Lys Gln His Glu
    130                 135                 140

Lys Glu Glu Phe Cys Gly Arg Pro Leu Gly Leu Arg Phe His Gly Glu
145                 150                 155                 160

Thr Gly Glu Leu Tyr Val Ala Asp Ala Tyr Tyr Gly Leu Met Val Val
                165                 170                 175

Gly Gln Ser Gly Gly Val Ala Ser Ser Val Ala Arg Glu Ala Asp Gly
            180                 185                 190

Asp Pro Ile Arg Phe Ala Asn Asp Leu Asp Val His Arg Asn Gly Ser
        195                 200                 205

Val Phe Phe Thr Asp Thr Ser Met Arg Tyr Ser Arg Lys Asp His Leu
    210                 215                 220

Asn Ile Leu Leu Glu Gly Glu Gly Thr Gly Arg Leu Leu Arg Tyr Asp
225                 230                 235                 240

Pro Glu Thr Ser Gly Val His Val Val Leu Lys Gly Leu Val Phe Pro
                245                 250                 255

Asn Gly Val Gln Ile Ser Glu Asp His Gln Phe Leu Leu Phe Ser Glu
            260                 265                 270

Thr Thr Asn Cys Arg Ile Met Arg Tyr Trp Leu Glu Gly Pro Arg Ala
        275                 280                 285

Gly Glu Val Glu Val Phe Ala Asn Leu Pro Gly Phe Pro Asp Asn Val
    290                 295                 300

Arg Ser Asn Gly Arg Gly Gln Phe Trp Val Ala Ile Asp Cys Cys Arg
305                 310                 315                 320

Thr Pro Ala Gln Glu Val Phe Ala Lys Arg Pro Trp Leu Arg Thr Leu
                325                 330                 335

Tyr Phe Lys Phe Pro Leu Ser Leu Lys Val Leu Thr Trp Lys Ala Ala
            340                 345                 350

Arg Arg Met His Thr Val Leu Ala Leu Leu Asp Gly Glu Gly Arg Val
        355                 360                 365

Val Glu Val Leu Glu Asp Arg Gly His Glu Val Met Lys Leu Val Ser
    370                 375                 380

Glu Val Arg Glu Val Gly Arg Lys Leu Trp Ile Gly Thr Val Ala His
385                 390                 395                 400

Asn His Ile Ala Thr Ile Pro Tyr Pro Leu Glu Asp
                405                 410


<210> SEQ ID NO 5
<211> LENGTH: 590
<212> TYPE: PRT
<213> ORGANISM: Zea mays

<400> SEQUENCE: 5

Met Arg Ala Leu Val Val Val Ser Phe Ala Ser Ala Cys Leu Leu Leu
1               5                   10                  15

Leu Leu Gln Leu Ala Gly Ala Ser His Val Val Tyr Asn Tyr Lys Asp
            20                  25                  30

Leu Glu Ala Glu Ala Ala Ala Ala Thr Asp Gln Val Pro Pro Ser Ile
        35                  40                  45

Val Asn Pro Leu Leu Arg Thr Gly Tyr His Phe Gln Pro Pro Lys Asn
    50                  55                  60

Trp Ile Asn Ala Pro Met Tyr Tyr Lys Gly Trp Tyr His Phe Phe Tyr
65                  70                  75                  80
```

-continued

```
Gln Tyr Asn Pro Lys Gly Ala Val Trp Gly Asn Ile Val Trp Ala His
                85                  90                  95

Ser Val Ser Arg Asp Leu Ile Asn Trp Val Ala Leu Glu Pro Ala Leu
            100                 105                 110

Arg Pro Ser Ile Pro Gly Asp Arg Tyr Gly Cys Trp Ser Gly Ser Ala
        115                 120                 125

Thr Val Leu Pro Asp Gly Gly Gly Pro Val Ile Met Tyr Thr Gly Val
    130                 135                 140

Asp His Pro Asp Ile Asn Tyr Gln Val Gln Asn Val Ala Tyr Pro Lys
145                 150                 155                 160

Asn Val Ser Asp Pro Leu Leu Arg Glu Trp Val Lys Pro Ser His Asn
                165                 170                 175

Pro Val Ile Val Pro Glu Gly Gly Ile Asn Ala Thr Gln Phe Arg Asp
            180                 185                 190

Pro Thr Thr Ala Trp Arg Gly Pro Gly Pro Glu Gln Trp Arg Leu Leu
        195                 200                 205

Val Gly Ser Ala Ala Gly Ser Ser Pro Arg Gly Val Ala Tyr Val Tyr
    210                 215                 220

Arg Ser Arg Asp Phe Arg Arg Trp Arg Arg Val Arg Arg Pro Leu His
225                 230                 235                 240

Ser Ala Ala Thr Gly Met Trp Glu Cys Pro Asp Phe Tyr Pro Val Ser
                245                 250                 255

Lys Gly Gly Ala Pro Arg Ala Gly Leu Glu Thr Ser Val Pro Pro Gly
            260                 265                 270

Pro Arg Val Lys His Val Leu Lys Asn Ser Leu Asp Leu Arg Arg Tyr
        275                 280                 285

Asp Tyr Tyr Thr Val Gly Thr Tyr His Pro Arg Ala Glu Arg Tyr Val
    290                 295                 300

Pro Asp Asp Pro Ala Gly Asp Glu His Arg Leu Arg Tyr Asp Tyr Gly
305                 310                 315                 320

Asn Phe Tyr Ala Ser Lys Thr Phe Tyr Asp Pro Ala Lys Arg Arg Arg
                325                 330                 335

Ile Leu Trp Gly Trp Ala Asn Glu Ser Asp Ser Ala Ala Asp Asp Val
            340                 345                 350

Ala Lys Gly Trp Ala Gly Ile Gln Ala Ile Pro Arg Thr Val Trp Leu
        355                 360                 365

Asp Pro Ser Gly Lys Gln Leu Leu Gln Trp Pro Ile Glu Glu Val Glu
    370                 375                 380

Ala Leu Arg Glu Lys Ser Val Thr Leu Lys Asn Arg Leu Ile Lys Ala
385                 390                 395                 400

Gly His His Val Glu Val Thr Gly Ile Gln Thr Ala Gln Ala Asp Val
                405                 410                 415

Glu Val Ser Phe Glu Val Ser Pro Ala Ala Leu Ala Gly Ala Glu Thr
            420                 425                 430

Leu Asp Pro Ala Leu Ala Tyr Asp Ala Glu Lys Leu Cys Gly Val Lys
        435                 440                 445

Arg Ala Asp Val Arg Gly Gly Val Gly Pro Phe Gly Leu Trp Val Leu
    450                 455                 460

Ala Ser Ala Asn Arg Lys Glu Arg Thr Ala Val Phe Phe Arg Val Phe
465                 470                 475                 480

Lys Pro Ala Ala Gly Ser Asp Lys Pro Val Val Leu Met Cys Thr Asp
                485                 490                 495

Pro Thr Lys Ser Ser Leu Asn Pro Asn Leu Tyr Arg Pro Thr Phe Ala
```

```
            500                 505                 510

Gly Phe Val Asp Thr Asp Ile Ser Asn Gly Lys Ile Ser Leu Arg Ser
        515                 520                 525

Leu Ile Asp Arg Ser Val Val Glu Ser Phe Gly Ala Gly Gly Lys Thr
    530                 535                 540

Cys Ile Leu Ser Arg Val Tyr Pro Ser Leu Ala Ile Gly Lys Asp Ala
545                 550                 555                 560

Arg Leu Tyr Val Phe Asn Asn Gly Arg Ala His Val Lys Val Ser Arg
                565                 570                 575

Leu Thr Ala Trp Glu Met Lys Lys Pro Val Met Asn Gly Ala
            580                 585                 590


<210> SEQ ID NO 6
<211> LENGTH: 1780
<212> TYPE: DNA
<213> ORGANISM: Artificial sequence
<220> FEATURE:
<223> OTHER INFORMATION: Synthetic sequence

<400> SEQUENCE: 6

gcaagcttca ccacccagtg tgatcgcata tccaatactc gttaagaaga ggaatgggag     60

ctggagtatg tgtgtcgatt acatgagcca taataaggcg tgtccaaaag atccactaca    120

atgcacattc gagcctagca accaggattc aattggacac cgagatgatg gacacatcga    180

tgtatacaca aatccaacag gtttggttga gcatgtgtgg ggacgtaatc atcgttagat    240

ttatgtaatt ttctattaat tattatgtaa ttttctaatt gtaatgtact ttttttaatt    300

attatgcact ttgtaatttt taatttaata aaaaatctat tatatatgtt ttatgatttg    360

taagcgttaa aaaaaatcta agtgattact taattatgaa atataaaagc tgatgtgcct    420

gtgagccgag gctataacct gtgtaggctg tacactggag cattagggac gagagtggag    480

tcgagagctg atgtggcagg tgcgagaaag tgatggtgca ctggcacata gtaaagacgg    540

attgtgacta ggctcaaggc gccaccacca ctgtctaaaa caagtcacac aagtttcaaa    600

cgtcttcttg ccgtgtctca cggaattgca acattcttgt cggaagacgc cactgtattc    660

acgggtaatc tcagcacgtt ataaagtgat gaggaacgcg gtcggaagtc ggaacaacca    720

ttggcatgta aagctccata tatgagtcgg tacaatatga tgtatatatg ccgatatgat    780

ggtgagaaca tcacaaaatg tacatcaagg gattaattgg gtgagaaaca aattgcgcgc    840

ctccgtgtac aatgaaatgg tgagtcacga gtcacgccga tctgatgtat atatgctaat    900

agctcgcacg acattgcaaa caactcatac cactacatta cagagttagt ttcatgaaaa    960

gcaagagtag gacggagtgg aaaataatcc ttgacgacgt gcacatgagc cacacgcaag   1020

agtactgaat aaatccagat gaaccctcca aaagtgaatg agatgagtca tatatacatt   1080

tggcaagaaa ccgtagaagc taccgccatc ggtttcatca tagaagaaga aattgtggta   1140

atcggaaagc tataaataac cgtcgtatgc ctatgcactt ttccaccacc accactggac   1200

gtcagcccat tagcttattg attgacgcag agaactcgac accatgaagg tgctgctcgt   1260

tgccctcgct ctcctggcgc tcgttgcaag cgccgcctcc actacaagcg gcggctgcgg   1320

ctgccagaca ccaccgtttc atctgccgcc tccgttctat ctgccgccgc cggtctacga   1380

gccgccgccg cagcagccgc agccatggca ataccccact caaccaccgc agctaagccc   1440

gtgccagcag ctcggatcct gcggcgtcgg cagcgtcgtc agcccgttcc tgggccagtg   1500

cgtcgagttc ctgaggcacc agtgcagccc ggcggcgacg ccctacggct cgccacagtg   1560
```

ccaggcgctg cagcagcagt gctgccacca gatcaggcgt ggtcctgcag tccttcctgc 1620
agcagcagcc gcagggcgag ctcgcggcgc tgatggcggc ccaggtagcg cagcagctga 1680
cggcgatgtg cggtctgcag ctgcagcagc agccaggtcc ctgcccttgc agcgcagctg 1740
ccggcggtgt ctactactga ggaaactatg ggtactgtag 1780

<210> SEQ ID NO 7
<211> LENGTH: 178
<212> TYPE: PRT
<213> ORGANISM: Zea mays

<400> SEQUENCE: 7

Met Lys Val Leu Leu Val Ala Leu Ala Leu Leu Ala Leu Val Ala Ser
1               5                   10                  15

Ala Ala Ser Thr Thr Ser Gly Gly Cys Gly Cys Gln Thr Pro Pro Phe
            20                  25                  30

His Leu Pro Pro Pro Phe Tyr Leu Pro Pro Pro Val Tyr Glu Pro Pro
        35                  40                  45

Pro Gln Gln Pro Gln Pro Trp Gln Tyr Pro Thr Gln Pro Pro Gln Leu
    50                  55                  60

Ser Pro Cys Gln Gln Leu Gly Ser Cys Gly Val Gly Ser Val Val Ser
65                  70                  75                  80

Pro Phe Leu Gly Gln Cys Val Glu Phe Leu Arg His Gln Cys Ser Pro
                85                  90                  95

Ala Ala Thr Pro Tyr Gly Ser Pro Gln Cys Gln Ala Leu Gln Gln Gln
            100                 105                 110

Cys Cys His Gln Ile Arg Arg Gly Pro Ala Val Leu Pro Ala Ala Ala
        115                 120                 125

Ala Ala Gly Arg Ala Arg Gly Ala Asp Gly Gly Pro Gly Ser Ala Ala
    130                 135                 140

Ala Asp Gly Asp Val Arg Ser Ala Ala Ala Ala Ala Ala Arg Ser Leu
145                 150                 155                 160

Pro Leu Gln Arg Ser Cys Arg Arg Cys Leu Leu Leu Arg Lys Leu Trp
                165                 170                 175

Val Leu

<210> SEQ ID NO 8
<211> LENGTH: 1239
<212> TYPE: DNA
<213> ORGANISM: Artificial sequence
<220> FEATURE:
<223> OTHER INFORMATION: Synthetic sequence

<400> SEQUENCE: 8
atggagaaga ggaacctgca gtggcggcga gggcgtgatg gcatcgtgca gtaccctcac 60
ctcttcttcg cggccctggc gctggccctc ctagtcgcgg acccgttcgg cctcagtccg 120
ctggccgagg tcgactaccg gccggtgaag cacgagctcg cgccgtacgg ggaggtcatg 180
ggcagctggc ccagagacaa tgccagccgg ctcaggcgcg ggaggctgga gttcgtcggc 240
gaggtgttcg ggccggagtc tatcgagttc gatctccagg gccgcgggcc gtacgccggc 300
ctcgccgacg gccgcgtcgt gcggtggatg ggcgaggagg ccgggtggga gacgttcgcc 360
gtcatgaatc ctgactggtc agaagaagtc tgtgccaatg gagtgaactc aacgacgagg 420
aagcagcacg agaaggagga gttctgcggc cggccgctcg gcctgaggtt ccacggggag 480
accggcgagc tctacgtcgc cgacgcgtac tacggtctca tggtcgttgg ccagagcggc 540

-continued

```
ggcgtggcgt cctccgtcgc gagggaagcc gacggggacc ccatccggtt cgcgaacgac    600

ctcgatgtgc acaggaatgg atccgtattc ttcactgaca cgagcatgag atacagcaga    660

aaggaccatc tgaacatcct gttagaagga gaaggcaccg ggaggctgct caggtatgat    720

ccagaaacaa gcggtgtcca tgtcgtgctc aaggggctgg tgttcccaaa cggcgtgcag    780

atctcagagg accatcagtt tcttctcttc tccgagacaa caaactgcag gataatgagg    840

tactggctgg aaggcccaag agcgggcgag gtagaggtgt tcgcgaacct gccgggcttc    900

cccgacaacg tgcgctccaa cggcaggggc cagttctggg tggcgatcga ctgctgccgg    960

acgccggcgc aggaggtgtt cgccaagagg ccgtggctcc ggaccctgta cttcaagttc   1020

ccgctgtcgc tcaaggtgct cacttggaag gccgccagga ggatgcacac ggtgctcgcg   1080

ctcctcgacg gcgaagggcg cgtcgtggag gtgctcgagg accggggcca cgaggtgatg   1140

aagctggtga gcgaggtgcg ggaggtgggc cgcaagctgt ggatcggaac cgtggcgcac   1200

aaccacatcg ccaccatccc ctacccttta gaggactaa                          1239


<210> SEQ ID NO 9
<211> LENGTH: 31
<212> TYPE: DNA
<213> ORGANISM: Artificial sequence
<220> FEATURE:
<223> OTHER INFORMATION: Ms45F primer

<400> SEQUENCE: 9

tgaattctgc tgagttctcc ttgggttatc c                                    31


<210> SEQ ID NO 10
<211> LENGTH: 28
<212> TYPE: DNA
<213> ORGANISM: Artificial sequence
<220> FEATURE:
<223> OTHER INFORMATION: Ms45R primer

<400> SEQUENCE: 10

tcccgggggt tgcgcatgaa ataggggt                                        28


<210> SEQ ID NO 11
<211> LENGTH: 28
<212> TYPE: DNA
<213> ORGANISM: Artificial sequence
<220> FEATURE:
<223> OTHER INFORMATION: Mn1pro bF primer

<400> SEQUENCE: 11

atcccgggct cgcatgagag aacaacca                                        28


<210> SEQ ID NO 12
<211> LENGTH: 30
<212> TYPE: DNA
<213> ORGANISM: Artificial sequence
<220> FEATURE:
<223> OTHER INFORMATION: Mnipro bR primer

<400> SEQUENCE: 12

gcaagcttgg gggtgctatt tgtactgtgc                                      30
```

METHOD FOR PROPAGATING STERILE MALE PLANT LINE

INCORPORATION BY REFERENCE TO ANY PRIORITY APPLICATIONS

Any and all applications for which priority claims are identified in the application data sheet, or any correction thereto, are hereby incorporated by reference, including the claim that this application is a divisional of U.S. application Ser. No. 14/437,633, filed Sep. 15, 2015 (now U.S. Pat. No. 10,246,723), which is the U.S. National Phase of International Application No. PCT/CN2013/001269, filed Oct. 18, 2013, designating the U.S. and published in Chinese as WO 2014/063442 on May 1, 2014, which claims the benefit of Chinese Patent Application No. 201210406154.1, filed Oct. 23, 2012 and Chinese Patent Application No. 201210406155.6, filed Oct. 23, 2012.

REFERENCE TO SEQUENCE LISTING

This application incorporates by reference the sequence listing submitted as ASCII text filed via EFS-Web on Sep. 15, 2015. The Sequence Listing is provided as a file entitled "30232494.TXT", created on Mar. 29, 2019 and is approximately 23.7 KB in size.

BACKGROUND OF THE INVENTION

Field of the Invention

The present invention relates to a new method for propagating a sterile male plant line, which uses a nuclear male sterility gene, a grain labeling gene, and a transgenic technique to propagate a sterile male plant line, belonging to the field of genetic plant breeding and seed production

Description of the Related Art

There is heterosis such that a hybrid has a considerable improvement in biomass, pest and disease resistance, stress (drought, high temperature, low temperature, saline-alkali soil, etc.) resistant capability over its parents; for example, hybrid corn (*zea mays*) or hybrid rice has a much greater production yield than homozygous parents thereof. A method often used for producing a hybrid comprises: growing a female parent and a male parent together, removing tassels of the female parent, while retaining tassels of the male parent, and harvesting seeds of the female parent as a hybrid.

There are three types of self-pollination, cross-pollination and often cross-pollination for plants in nature. Self-pollination refers to a phenomenon where gynoecia of a plant are pollinated with pollen from the same plant. Among plants with a hermaphrodite flower, it may be classified into autogamy in which pollination occurs between stamen and pistil of a single flower (*phaseolus*); gei-tonogany in which pollination occurs between different followers in the same inflorescence (individual); and close pollination in which pollination occurs between different followers in the same plant. Some plants have stamen and pistil grown not in the same flower, even not in the same plant, incapable of self-pollination, and their pistil can merely receive pollen from other flower—this is called cross-pollination. A type of crops that has a natural hybridization rate of greater than 50% and declined selfing is classified into often cross-pollinated crops, such as corn.

Corn is an androgynal plant, and has female and male flowers at different positions of a plant. Corn can propagate via self-pollination or cross-pollination, and finish its natural pollination when pollen is blown from tassels to filaments of female ears in natural conditions.

In breeding of corn, a self-bred line of homozygous corn should be first developed, then two self-bred lines are crossed, and the progenies thereof are assessed for yield, resistance, etc., to determine the presence of a commercialization potential or not. Therein, each of the self-bred lines may have one or more good traits of which another self-bred line lacks, or complement one or more poor traits another self-bred line has. Hybridization of two self-bred lines results in a seed of a first generation, called the F1 seed, which is germinated to obtain a F1 plant. The F1 plant is stronger than both of parental (paternal and maternal) self-bred lines, while simultaneously having greater biomass.

A hybrid may be produced by artificial emasculation of the female parent, i.e., removal of tassels of un-pollinated female parents (which may be sown in a field alternated with the male parent, for example, by sowing 5 rows of the female parent with 1 row of the male parent), remaining tassels of male parents. Subsequently, with only an isolation of foreign corn pollen, female ears of the female parent may merely receive pollen from the male parent, to obtain a seed, i.e., a hybrid seed (F1). Such hybrid seeds may be used for agricultural production.

In the production of the hybrid seeds, a plant may be tassellized again after emasculation due to a change in environment, or may be incompletely emasculated, both of which may lead to a self-pollination of the female parent, so that produced hybrid seeds have the seeds from the maternal self-bred line blended. The yield of the maternal self-bred line is much lower than that of the hybrid seed, and such a seed is an unqualified product, which will have an adverse impact on the income of a farmer and on the credit of a seed producing company, and more severely the seed producing company will have to assume corresponding liability to pay compensation.

Machines may also be used for emasculation of the female parent, emasculation by machine is reliable substantially the same as manual emasculation, but faster and with lower costs. However, in comparison with manual emasculation, most of machines for emasculation will make more damage on a plant. For this reason, there is no means completely satisfied for emasculation by now, and there is still a need of an alternating method with lower costs and more complete emasculation.

A stable male sterility system provides a simple and effective method, and onerous emasculation may be obviated in some genotypes by using a nucleo-cytoplasmic interacting male sterile (CMS) self-bred line. This method comprises three main materials, i.e., a sterile line: a male sterility material; a maintainer line: capable of providing pollen to the sterile line, allowing progenies of the sterile line still to be a sterile line, a restorer line: capable of restoring fertility of a sterile line. The sterile line is crossed with the restorer line to produce F1, i.e., a hybrid seed used for agricultural production. More particularly, a nucleo-cytoplasmic interacting sterility type is characterized by heredity of nucleo-cytoplasmic interaction. It is required not only that the cytoplasma has a sterility gene S, but also that the nucleus has a homozygous sterility gene (rfrf), and only in the presence of both, a plant may exhibit male sterility. If the cytoplasmic gene is a fertile N, the plant will exhibit male fertility regardless of fertility (RfRf) or sterility (rfrf) of the nucleic gene. Similarly, if the nucleus has a fertility gene (RfRf) or (Rfrf), the plant will exhibit male fertility regardless of fertility N or sterility S of the cytoplasmic gene. Such a male sterile line formed from a nucleo-cytoplasmic interaction is genetically composed of S (rfrf), which cannot produce normal pollen, but can parent for hybridization. Since a maintainer line N (rfrf) [which is used to cross with a sterile line to produce F1 that is still able to maintain male sterility, that is: S (rfrf) (♀)×N (rfrf)→S (rfrf) (sterility)] may be found and may receive pollen from a restorer line S(RfRf) or N(RfRf) [which is used to cross with a sterile line to produce F1 that is fertile, that is: S (rfrf) (♀)×S (RfRf)→S (Rfrf) (F1) (fertile), or S (rfrf) (♀)×N (RfRf)→S (Rfrf) (F1) (fertile)], to restore F1 to be male fertile, F1 plant may be self-bred to generate F2. Therefore, this may be widely used in agricultural production. The use of male sterile line may avoid manual emasculation, save manpower and reduce seed cost, and guarantee purity of seeds. Currently, nucleo-cytoplasmic interacting male sterility has been used for the production of hybrid seeds in crops such as rice, corn, *Sorghum*, onion, castor, sugarbeet and rape; for the nucleo-cytoplasmic interacting male sterile line of additional crops, wide studies are also on the way.

CMS system also has its drawbacks. One is an observation that individual CMS materials are susceptible. Another one is difficulty in finding restorer line. These problems prevent wide use of the CMS system in seed production.

U.S. Pat. Nos. 4,654,465 and 4,727,219 to Brar et al. disclose a type of genetic sterility. However, this type of genetic sterility requires maintaining of corresponding genotypes at a number of different sites within a genome, and labeling, tracing and detecting of these sites in each generation. Patterson also describes a possibly useful chromosomal translocation gene system, however, this system is more complex (see U.S. Pat. Nos. 3,861,709 and 3,710,511).

People have been trying to optimize the male sterility system. For example, Fabijanski, et al. developed a method of making a male sterile plant (EPO 89/3010153.8 with a Publication No. 329308 and PCT Application No. PCT/CA90/00037 published as WO 90/08828). Fertility of a male flower of a plant is inhibited primarily by following two methods. One is to link a promoter specifically expressed by a male tissue to a cytotoxic gene and transplant it into a plant, so that the male flower cannot pollinate as normal and does not affect other traits; the other is, by gene interfering means, to interfere a cloned gene for regulating male flower fertility of a plant in a transgenic way, so that it is not capable of normally functioning. Additionally, there are means to inhibit gene expression through some gene regulatory elements, so as to affect fertility of a plant (WO90/08829).

In most cases, only a plant with a male sterility regulatory nuclear gene that is homozygous recessive (msms) will exhibit male sterility. Since a male sterile plant is not capable of selfing, the male sterile plant (msms) may be obtained only by its cross with a heterozygous plant (Msms). And, there are both of male sterile grains (msms) and fertile heterozygous grains (Msms) on the same ear, from which it is impossible to distinguish which are sterile grains, and which are fertile grains. Those may be distinguished only at the time of pollination of the plant after sowing.

Recently, transgenic methods are also used to keep sterility of a male sterile plant (U.S. Pat. No. 6,743,968). Such methods construct a pollen lethal gene and a male fertility restorer gene into a single vector, and introduce it into a male sterile plant. Transgenic progenies exhibit fertility, but having only ability of producing pollen free of a restorer gene. When such a plant is crossed with a male sterile plant, a recessive sterile plant is maintained in a homozygous recessive state. First, a transgenic vector is constructed, which contains a pollen cell lethal gene and meanwhile a dominant gene of restoring plant fertility. The vector is introduced into a male sterile plant, and is present in the transgenic plant in a heterozygous state. The plant is fertile due to the presence of the fertility restorer gene, and when it is crossed with a male sterile plant, pollen (Msms) containing both of a restorer gene and a lethal gene results in pollen abortion. Therefore, only the pollen (ms) containing no restorer gene can be crossed with a female gamete (ms) of a male sterile plant, and each of the progenies is a homozygous recessive individual (msms).

As previously described, an important problem in many attempts for seed production with a male sterility system is how to use the male sterility gene and how to distinguish a male sterile seed and a fertile seed, while considering how to maintain the sterility of a sterile individual.

Many male sterile mutants have been identified in corn (Skibbe et al. 2005), particularly as seen in the table below:

TABLE 1

Male sterile mutants resulted from a nuclear gene

| Mutant (allelic mutation) | Chromosome | References |
|---|---|---|
| ms1 | 6 | Singleton W. R and Jonnes D. F. 1930. Heritable characters of maize. XXXV. Male sterile. J Hered 21: 266-268 |
| ms2 | 9 | Eyster W. H. 1931. J Hered 22: 99-102; ALBERTSEN M. C., R. L. PHILLIPS, 1981. Developmental cytology of 13 genetic male sterile loci in maize. Can. J. Genet. Cytol. 23: 195-208 |
| ms3 | 3 | Eyster W. H. 1931. J Hered 22: 99-102 |
| ms4(po1) | | BEADLE G. W., 1932. GENES IN MAIZE FOR POLLEN STERILITY. GENETICS17: 413-431 |
| ms5 | 5 | BEADLE G. W., 1932. GENES IN MAIZE FOR POLLEN STERILITY. GENETICS17: 413-431; ALBERTSEN M. C., R. L. PHILLIPS, 1981. Developmental cytology of 13 genetic male sterile loci in maize. Can. J. Genet. Cytol. 23: 195-208 |
| ms6(po1) | | BEADLE G. W., 1932. GENES IN MAIZE FOR POLLEN STERILITY. GENETICS17: 413-431; ALBERTSEN M. C., R. L. PHILLIPS, 1981. Developmental cytology of 13 genetic male sterile loci in maize. Can. J. Genet. Cytol. 23: 195-208 |

TABLE 1-continued

| Male sterile mutants resulted from a nuclear gene | | |
|---|---|---|
| Mutant (allelic mutation) | Chromosome | References |
| ms7 | 7 | BEADLE G. W., 1932. GENES IN MAIZE FOR POLLEN STERILITY. GENETICS17: 413-431; ALBERTSEN M. C., R. L. PHILLIPS, 1981. Developmental cytology of 13 genetic male sterile loci in maize. Can. J. Genet. Cytol. 23: 195-208 |
| ms8 | 8 | BEADLE G. W., 1932. GENES IN MAIZE FOR POLLEN STERILITY. GENETICS17: 413-431; ALBERTSEN M. C., R. L. PHILLIPS, 1981. Developmental cytology of 13 genetic male sterile loci in maize. Can. J. Genet. Cytol. 23: 195-208 |
| ms9 | 1 | BEADLE G. W., 1932. GENES IN MAIZE FOR POLLEN STERILITY. GENETICS17: 413-431; ALBERTSEN M. C., R. L. PHILLIPS, 1981. Developmental cytology of 13 genetic male sterile loci in maize. Can. J. Genet. Cytol. 23: 195-208 |
| ms10 | 10 | BEADLE G. W., 1932. GENES IN MAIZE FOR POLLEN STERILITY. GENETICS17: 413-431; ALBERTSEN M. C., R. L. PHILLIPS, 1981. Developmental cytology of 13 genetic male sterile loci in maize. Can. J. Genet. Cytol. 23: 195-208 |
| ms11 | 10 | BEADLE G. W., 1932. GENES IN MAIZE FOR POLLEN STERILITY. GENETICS17: 413-431; ALBERTSEN M. C., R. L. PHILLIPS, 1981. Developmental cytology of 13 genetic male sterile loci in maize. Can. J. Genet. Cytol. 23: 195-208 |
| ms12 | 1 | BEADLE G. W., 1932. GENES IN MAIZE FOR POLLEN STERILITY. GENETICS17: 413-431; ALBERTSEN M. C., R. L. PHILLIPS, 1981. Developmental cytology of 13 genetic male sterile loci in maize. Can. J. Genet. Cytol. 23: 195-208 |
| ms13 | 5 | BEADLE G. W., 1932. GENES IN MAIZE FOR POLLEN STERILITY. GENETICS17: 413-431; ALBERTSEN M. C., R. L. PHILLIPS, 1981. Developmental cytology of 13 genetic male sterile loci in maize. Can. J. Genet. Cytol. 23: 195-208 |
| ms14 | 1 | BEADLE G. W., 1932. GENES IN MAIZE FOR POLLEN STERILITY. GENETICS17: 413-431; ALBERTSEN M. C., R. L. PHILLIPS, 1981. Developmental cytology of 13 genetic male sterile loci in maize. Can. J. Genet. Cytol. 23: 195-208 |
| ms15 | | BEADLE G. W., 1932. GENES IN MAIZE FOR POLLEN STERILITY. GENETICS17: 413-431 |
| ms16 | | BEADLE G. W., 1932. GENES IN MAIZE FOR POLLEN STERILITY. GENETICS17: 413-431 |
| ms17 | 1 | EMERSON R. A., 1932. A recessive zygotic lethal resulting in 2:1 ratios for normal vs. male-sterile and colored vs. colorless pericarp in F2 of certain maize inbreds. Science 75: 566; ALBERTSEN M. C., R. L. PHILLIPS, 1981. Developmental cytology of 13 genetic male sterile loci in maize. Can. J. Genet. Cytol. 23:195-208 |
| ms18 | 1 | EYSTER W. H., 1934. Genetics of Zeamays. Bibliogr. Genet. 11: 187-392 |
| ms19 | 9 | EYSTER W. H., 1934. Genetics of Zeamays. Bibliogr. Genet. 11: 187-392 |
| ms20 | | EYSTER W. H., 1934. Genetics of Zeamays. Bibliogr. Genet. 11: 187-392 |
| Ms21 | 6 | SCHWARTZ D., 1951 . The interaction of nuclear and cytoplasmic factors in the inheritance of male sterility in maize. Genetics 36: 676-696 |
| ms22 (msca1) | 7 | WEST D. R., M. C. ALBERTSEN, 1985. Three new male-sterility genes. MaizeGenet. Coop. Newsletter 59: 87; TRIMNELL M. R., T. W. FOX, M. C. ALBERTSEN, 2001 New male-sterilemutant allele of Ms22. Maize Genet. Coop. Newsletter 75: 31; CHAUBAL R., J. R. ANDERSON, M. R. TRIMNELL, T. W. FOX, M. C. ALBERTSEN, P. BEDINTGER, 2003. The transformation of anthers in themscal mutant of maize. Planta 216: 778-788 |
| ms23 | | WEST D. R., M. C. ALBERTSEN, 1985. Three new male-sterility genes. Maize Genet. Coop. Newsletter 59: 87; CHAUBAL R., C. ZANELLA, M. R. TRIMNELL, T. W. FOX, M. C. ALBERTSEN, P. BEDINGER, 2000. Two male-sterile mutants of Zea mays (Poaceae) with an extra cell division in the anther wall. Am. J. Bot. 87: 1193-1201 |

TABLE 1-continued

| Male sterile mutants resulted from a nuclear gene | | |
|---|---|---|
| Mutant (allelic mutation) | Chromosome | References |
| ms24 | 10 | WEST D. R., M. C. ALBERTSEN, 1985. Three new male-sterility genes. Maize Genet. Coop. Newsletter 59: 87; FOX T. W., M. R. TRIMNELL, M. C. ALBERTSEN, 2002. Male-sterile mutant ms24 mapped to chromosome 10. Maize Genet. Coop. Newsletter 76: 37 |
| ms25 | 9 | LOUKIDES C. A., A. H. BROADWATER, P. A. BEDINGER, 1995. Two newmale-sterile mutants of Zea mays (Poaceae) with abnormal tapetal cell morphology. Am. J. Bot. 82: 1017-1023 |
| ms26 | 1 | LOUKIDES C. A., A. H. BROADWATER, P. A. BEDINGER, 1995. Two newmale-sterile mutants of Zea mays (Poaceae) with abnormal tapetal cell morphology. Am. J. Bot. 82: 1017-1023 |
| ms27 | | ALBERTSEN M. C., 1996. Ms-gene designations. Maize Genet. Coop. Newsletter 70: 30-31 |
| ms28 | 1 | GOLUBOVSKAYA I. N., D. V. SITNIKOVA, 1980. Three meiotic mutations of maize, causing irregular segregation of chromosomes in the first division of meiosis. Genetika 16: 656-666 |
| ms29 | 10 | TRIMNELL M. R., T. W. FOX, M. C. ALBERTSEN, 1998. New chromosome 10S male-sterile mutant: ms29. Maize Genet. Coop. Newsletter 72: 37-38 |
| ms30 (msx) | 4 | TRIMNELL M. R., T. W. FOX, M. C. ALBERTSEN, 1998. New chromosome 2L male-sterile mutants ms30 and ms31. Maize Genet. Coop. Newsletter 72: 38 |
| ms31 | 2 | TRIMNELL M. R., T. W. FOX, M. C. ALBERTSEN, 1998. New chromosome 2L male-sterile mutants ms30 and ms31. Maize Genet. Coop. Newsletter 72: 38 |
| ms32 | 2 | CHAUBAL R., C. ZANELLA, M. R. TRIMNELL, T. W. FOX, M. C. ALBERTSEN, P. BEDINGER, 2000. Two male-sterile mutants of Zea mays (Poaceae) with an extra cell division in the anther wall. Am. J. Bot. 87: 1193-1201 |
| ms33 | 2 | TRIMNELL M. R., E. PATTERSON, T. W. FOX, P. BEDINGER, M. C. ALBERTSEN, 1999. New chromosome 2L male-sterile mutantms33 and alleles. Maize Genet. Coop. Newsletter 73: 48-49 |
| ms34 | 7 | TRIMNELL M. R., E. PATTERSON, M. C. ALBERTSEN, 1999. New chromosome 7L male-sterile mutant ms34. Maize Genet. Coop. Newsletter 73: 49 |
| ms35 (ms23) | | TRIMNELL M. R., E. PATTERSON, T. W. FOX, M. C. ALBERTSEN, 1999. New chromosome 9L male-sterile mutants ms35 and ms36. Maize Genet. Coop. Newsletter 73: 49-50; TRIMNELL M. R., T. W. FOX, M. C. ALBERTSEN, 2002. We made a mistake! ms35 is allelic to ms23, but what is the correct map location? Maize Genet. Coop. Newsletter 76: 37-38; ALBERTSEN M. C., T. W. FOX, M. R. TRIMNELL, 1999 . Changing a duplicated designation for two different male-sterile mutations Maize Genet. Coop. Newsletter 73: 48 |
| ms36 | 9 | TRIMNELL M. R., E. PATTERSON, T. W. FOX, M. C. ALBERTSEN, 1999. New chromosome 9L male-sterile mutants ms35 and ms36. Maize Genet. Coop. Newsletter 73: 49-5 |
| ms37 | 3 | TRIMNELL M. R., T. W. FOX, M. C. ALBERTSEN, 1999. New chromosome 3L male-sterile mutant ms37. Maize Genet. Coop. Newsletter 73: 48 |
| ms38 (ms*WL89A) | 2 | TRIMNELL M. R., T. W. FOX, M. C. ALBERTSEN, 1998a New chromosome 10S male-sterile mutant: ms29. Maize Genet. Coop. Newsletter 72: 37-38; ALBERTSEN M. C., T. W. FOX, M. R. TRIMNELL, 1999. Changing a duplicated designation for two different male-sterile mutations Maize Genet. Coop. Newsletter 73: 48 |
| Ms41 | 4 | NEUFFER M. G., 1987. Location of dominant male sterile on chromosome 4L. Maize Genet. Coop. Newsletter 61: 51 |
| Ms42 | 5 | ALBERTSEN M. C., T. W. FOX, M. R. TRIMNELL, M. G. NEUFFER, 1993. Interval mapping a new dominant male-sterile mutant, Ms42. Maize Genet. Coop. Newsletter 67: 64 |
| ms43 | 8 | GOLUBOVSKAYA I. N., 1979 . Genetical control of meiosis. Int. Rev. Cytol. 58: 247-290 |

TABLE 1-continued

| Male sterile mutants resulted from a nuclear gene | | |
|---|---|---|
| Mutant (allelic mutation) | Chromosome | References |
| Ms44 | 4 | ALBERTSEN M. C., L. M. SELLNER, 1988. An independent, EMS-induced dominant male sterile that maps similar to Ms41. Maize Genet. Coop. Newsletter 62: 70; ALBERTSEN M. C., M. G. NEUFFER, 1990. Dominant male sterile in maize. Maize Genet. Coop. Newsletter 64: 52 |
| ms45 | 9 | ALBERTSEN M. C., M. R. TRIMNELL, T. W. FOX, 1993. Tagging, cloning and characterizing a male fertility gene in maize. Am. J. Bot. 80: 16 |
| ms47 | 10 | TRIMNELL M. R., T. W. FOX, M. C. ALBERTSEN, 2002. New chromosome 10 male-sterile mutant: ms47. Maize Genet. Coop. Newsletter 76: 38 |
| ms48 | 9 | TRIMNELL M. R., T. W. FOX, M. C. ALBERTSEN, 2002. New chromosome 9L male-sterile mutant: ms48. Maize Genet. Coop. Newsletter 76: 38 |
| ms49 | 10 | TRIMNELL M. R., T. W. FOX, M. C. ALBERTSEN, 2002. New chromosome 10 male-sterile mutant: ms49. Maize Genet. Coop. Newsletter 76: 38-39 |
| ms50 | 6 | TRIMNELL M. R., T. W. FOX, M. C. ALBERTSEN, 2002e New chromosome 6L male-sterile mutant: ms50. Maize Genet. Coop. Newsletter 76: 39 |
| ms52 | 10 | Skibbe DS, Schnable PS: Male sterility in maize. Maydica 2005, 50: 367-376 |

These genes as above have been successively cloned, e.g., ms45 (Albertsen et al. 1993) and ms26 (PTC/US2006/024273). Meanwhile, some male sterility genes from rice also have been successively cloned, e.g., dpw (Jing Shi et al. 2011), and some male sterility genes, e.g., (Aarts, et al. 1993) have been identified in *Arabidopsis.*

SUMMARY OF THE INVENTION

The present invention provides a method for propagating a sterile male plant line, to maintain a male sterile plant in a homozygous recessive state, the method comprising:

(a) providing a first plant that comprises a homozygous recessive male sterility allele;

(b) providing a second plant, comprising a homozygous recessive male sterility allele the same as that in the first plant, and a construct, wherein the construct exists in a heterozygous state in the second plant and comprises:

i. a first nucleotide sequence that will restore the male fertility of the first plant when it is expressed in the first plant;

ii. a second nucleotide sequence that is able to affect the grain shape or the endosperm nutrient material composition in a heterozygous state, which allows for distinguishing the grains with or without said construct by observation through naked eyes or devices;

wherein the first nucleotide sequence and the second nucleotide sequence are tightly linked with each other and coexist in the plant;

(c) fertilizing the female gametes of the first plant with the male gametes of the second plant, to produce progenies maintaining the homozygous recessive state of the first plant.

In above method, the grain shape may be characterized by size, length, width and/or thickness, etc.; the endosperm nutrient material composition may be presence or absence of farinaceous endosperm, starch content and/or oil content, etc.

In above method, each of the plants, the first plant and the second plant may be a monocotyledonous plant or a dicotyledonous plant, such as corn, rice, *Sorghum*, wheat, soybean, cotton or sunflower.

In above method, the first nucleotide sequence comprises a male fertility regulatory gene, e.g., a wild-type allele, Ms45, of ms45 in Table 1. The male fertility regulatory gene is not limited to the genes listed in Table 1, and male fertility regulatory genes in corn or other species may also achieve the purpose of the present invention, and therefore are also within the scope of the present invention.

In an example of the present invention, the first plant is a male sterile mutant, ms45, of corn; and/or, The first nucleotide sequence is an Ms45 expression element; the Ms45 expression element expresses protein Ms45 as presented by SEQ ID No: 4 in the first plant.

Therein, SEQ ID No: 4 consists of 412 amino acids.

In an example of the present invention, the Ms45 expression element has an Ms45 encoding sequence of SEQ ID No: 8. The Ms45 expression element has a nucleotide sequence of SEQ ID No: 1, comprising a promoter and a gene, wherein positions 8-542 of SEQ ID No:1 represents the sequence of the promoter, and positions 1422-2972 of SEQ ID No:1 represents ORF.

In an example of the present invention, the inventors construct a plant expression vector containing the Ms45 expression element as presented by SEQ ID No: 1, and transform the vector into a male sterile mutant ms45, allowing for restoring the fertility of the mutant.

In an embodiment of the present invention, the second nucleotide sequence in the second plant in a heterozygous state affects the size of the grains of the second plant.

In an example of the present invention, the second nucleotide sequence is a DNA fragment that interferes the expression of the protein of SEQ ID No: 5.

Therein, SEQ ID No: 5 consists of 590 amino acid residues, which is the amino acid sequence of protein Mn1.

In an example of the present invention, the DNA fragment that interferes the expression of the protein of SEQ ID No: 5 may be $SEQ_{for}$-X-$SEQ_{rev}$;

The nucleotide sequence of $SEQ_{for}$ is positions 14-276 of SEQ ID No: 2; the sequence of $SEQ_{rev}$ is reversely complementary with that of $SEQ_{for}$; the X is a spacer sequence between the $SEQ_{for}$ and the $SEQ_{rev}$, and is not complementary with the $SEQ_{for}$ and the $SEQ_{rev}$ in sequence.

The nucleotide sequence of $SEQ_{for}$-X-$SEQ_{rev}$ may be positions 14-663 of SEQ ID No: 2.

Therein, SEQ ID No: 2 is a Mn1 interference fragment, Mn1RNAi, for silencing Mn1 gene, and consists of 675 nucleotides. SEQ ID No:2 has positions 7-13 as a Bst EII recognition sequence, positions 14-276 as a nucleotide sequence of Mn1$SEQ_{for}$, positions 277-400 as X, an intron forming a hairpin structure, positions 401-663 as a nucleotide sequence of Mn1$SEQ_{rev}$, and positions 664-669 as a Hind III recognition sequence.

In another embodiment of the present invention, the second nucleotide sequence in the second plant, when exists in a heterozygous state, affects the grains of the second plant with or without farinaceous endosperm.

In an example of the present invention, the second nucleotide sequence encodes Mc16-KDγ-prolamin of SEQ ID No: 7, wherein SEQ ID No: 7 consists of 178 amino acids.

In the second nucleotide sequence, the gene of Mc16-KDγ-prolamin is positions 1244-1780 of SEQ ID No: 6.

Therein, SEQ ID No: 6 consists of 1780 nucleotides, having positions 9-1149 as a promoter sequence, positions 1244-1780 as Mc16-KDγ-prolamin encoding gene sequence, encoding Mc16-KDγ-prolamin of SEQ ID No:7.

The second nucleotide sequence is particularly as presented by SEQ ID No: 6.

The present invention also seeks for the construct (a DNA construct) in above method, the second plant, and the homozygous recessive male sterile plant produced using above method.

Aforementioned DNA construct may restore the fertility of a male sterile mutant, while changing grain shape (e.g., size, length, width, thickness, etc.) or changing grain endosperm nutrient material composition (e.g., starch content, oil content, presence or absence of farinaceous endosperm, etc.).

Aforementioned second plant may maintain the sterility of a male sterile plant.

Tissue culture of regenerative cells produced by the second plant in above method and protoplast produced in the tissue culture also belong to the scope of the present invention.

The plant as described above may be all or part of the plant, such as a seed, a root, a stem, a leaf, an embryo, an apical, pollen, or an anther, or the like.

In the present invention, the inventors establish an effective, new method for propagating a sterile male plant line by taking use of a plant male fertility regulatory gene, a grain labeling gene and a transgenic technique. In an embodiment of the present invention, the seed labeling gene is nucleotides to regulate grain with a special shape (e.g., size, length, width, thickness, etc.); in another embodiment of the present invention, the seed labeling gene is nucleotides to regulate main endosperm nutrient material composition (e.g., starch content, oil content, the present or absence of farinaceous endosperm, etc.).

In the present invention, a wild-type nucleotide sequence regulating male fertility and a nucleotide sequence regulating grain shape or grain endosperm nutrient material composition are linked, and transformed into a conventional corn, which is then backcrossed to a plant of a homozygous recessive male sterile line, to obtain a transgenic plant; the transgenic plant is crossed with a homozygous recessive sterile line, allowing for obtaining a large number of seeds of both a sterile line and a maintainer line. Due to the regulation of grain shape or grain endosperm nutrient material composition by the nucleotide sequences, the sterile line and the maintainer line may be distinguished through grain shape or endosperm composition. Therein, seeds with a normal shape or a normal endosperm composition belongs to a sterile line (free of transgenic sequence), and those with an abnormal shape (e.g., a variation in grain size, length, width, thickness, etc.) or an abnormal endosperm composition (e.g., a variation in starch content, oil content, present or absence of farinaceous endosperm) belong to a maintainer line.

In an embodiment of the present invention, the inventors construct a plant transforming vector, which comprises an expression element for a male fertility restoring gene and an expression element for a grain shape (e.g., size, length, width, thickness, etc.) regulating gene, while the gene regulating grain shape (e.g., size, length, width, thickness, etc.) is a dominant gene or a fragment of an interference sequence. The vector is transformed into HiIIAxHiIIB corn hybrid to obtain a transgenic plant, which is then backcrossed with a male sterile plant, so as to introduce the nucleotide sequences regulating the male fertility and grain specific shape (e.g., size, length, width, thickness, etc.) of a plant into the male sterile plant. Due to the presence of a restorer gene, the plant exhibits fertility. When the transgenic heterozygous plant (Msmsms) is crossed with a male sterile plant (msms), two progenies will be produced, one being male sterile grains with normal grains (a sterile line, with a genotype of msms), which may restore fertility with any of wild-type plants; the other being fertile grains with abnormal grains (a maintainer line, with a genotype of Msmsms), which has homozygous recessive sites that regulate male fertility. As a result of inclusion of the transgenic sequence that is complementary, the plant exhibits fertility; and in virtue of also comprising the nucleotide sequence that affects grain shape (e.g., size, length, width, thickness, etc.), it has a grain shape (e.g., size, length, width, thickness, etc.) different than that of a wild-type.

In another embodiment of the present invention, the inventors construct a plant transforming vector, which comprises an expression element for a male fertility restoring gene and an expression element for a gene regulating main nutrient material composition (e.g., starch content, oil content, presence or absence of farinaceous endosperm, etc.) of endosperm, wherein the gene regulating the main nutrient material composition (e.g., starch content, oil content, presence or absence of farinaceous endosperm, etc.) of endosperm is a dominant gene or a fragment of an interference sequence. The vector is transformed into an HiIIAxHiIIB corn hybrid, to obtain a transgenic plant, which is then backcrossed with a male sterile plant, so as to introduce both of the nucleotide sequences regulating male fertility and main endosperm nutrient material composition (e.g., starch content, oil content, presence or absence of farinaceous endosperm, etc.) of a plant into the male sterile plant. Due to the presence of a restorer gene, the plant exhibits fertility. When the transgenic heterozygous plant (Msmsms) is crossed with a male sterile plant (msms), two progenies will be produced, one being male sterile grains with normal endosperm (a sterile line, with a genotype of msms), which may have fertility restored with any of wild-type plants; the other being fertile grains with abnormal endosperm (a maintainer line, with a genotype of Msmsms), which may have homozygous recessive sites for regulating male fertility. As a result of inclusion of the transgenic sequence that is complementary, the plant exhibits fertility; and in virtue of also comprising the nucleotide sequence that affects main endosperm nutrient material composition (e.g., starch content, oil content, presence or absence of farinaceous endosperm, etc.), it has a main endosperm nutrient material composition (e.g., starch content, oil content, presence or absence of farinaceous endosperm, etc.) different than that of a wild-type.

Additional goals of the present invention will be obvious from following description and claims.

DETAILED DESCRIPTION OF THE PREFERRED EMBODIMENT

All the technical and scientific terms used herein have meanings as commonly understood by those ordinary skilled in the art to which the present invention belongs, unless otherwise specifically indicated. The techniques used and mentioned herein are standard techniques recognized by those ordinary skilled in the art, and the materials, methods and examples are provided only by way of illustration, rather than limiting.

Nuclear male sterility is a result of a key gene that is mutated, inhibited or otherwise affected during the formation of microspores, and such a gene is generally referred to as a male sterility gene. The pollen developing pathway is regulated by various genes, and thus there are many genes whose mutation will finally result in male sterility. Currently, a large number of male sterile mutants (as shown in Table 1) have been identified in corn plants, and each of the male sterility genes has its specific restorer gene, that is, each of the male sterile mutants can be restored only with its wild-type allele.

Figure 1:
FIG. 1 shows male flower phenotypes of a male fertile mutant ms45 and a wild-type Ms45.

In the present invention, taking a corn male sterile mutant, such as ms45, in Table 1 as an example, the mutant has a male flower unable of normal pollination (as shown in FIG. 1, the left plant is a male sterile mutant, and the right plant is a wild-type), and the fertility of the mutant may be restored with a wild-type plant. In the present invention, a wild-type restorer gene is derived from a self-bred line B73, with a sequence presented by SEQ ID No: 1. The sequence comprises promoter (positions 8-542 of SEQ ID No: 1) and ORF (positions 1422-2972 of SEQ ID No: 1) sequences of a Ms45 gene. After transformation of DNA as presented by SEQ ID No: 1 into an ms45 male sterile mutant, the mutant plant exhibits fertility.

Figure 2:
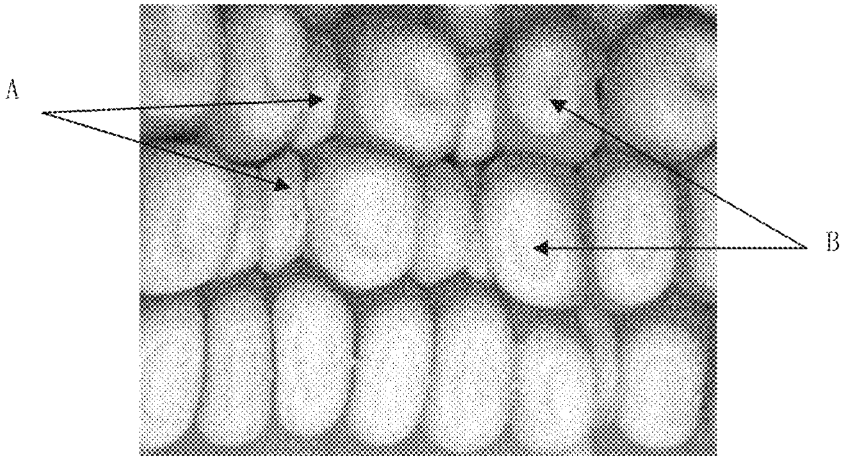
FIG. 2 shows grain phenotypes of a grain size regulating gene Mn1 mutant and a wild-type.

In an embodiment of the present invention, the present invention constructs a plant expression interfering vector of a gene of corn endosperm-specific cell wall invertase, CWI-2 (Cheng, W H et al. 1996), to silence the gene. The mutant of the gene is designated as miniature1 (mn1), and a mutation or silence of the gene will result in smaller grains. Since the gene is specifically expressed in endosperm, silence of the gene will not affect other traits of the same plant. During fertilization of a corn plant, a fertilized gamete comprising the vector will affect endosperm development, thereby resulting in smaller grains. Mn1 gene encodes a cell wall invertase, and if inactivated, will have an influence on the development of grain endosperm to result in smaller grains (as shown in FIG. 2, A is a mn1 mutant grain, and B is a wild-type grain), but have no impact on the development of embryo and the plant. Most of Mn1 mutants in nature or from artificial mutagenesis are recessive mutants. The inventors interferes a wild-type Mn1 gene at a mRNA level with a transgenic technique, so that grains will become smaller as long as having a transformed interference nucleotide fragment, as indicated by A in FIG. 4. Therefore, when the transformed fragment exists in a grain in a heterozygous state, the grain having the transformed fragment may be quickly distinguished in terms of grain size. Likewise, a similar operation may also be performed on other gene(s) that affects the development of grain shape (e.g., size, length, width, thickness, etc.) by the same method, to obtain an easily distinguishable transgenic grain. The RNAi interference sequence of Mn1 gene in the present invention is derived from B73, but not limited to self-bred line B73, and may be likewise derived from any other wild-type corn self-bred line, or a homologous gene from another species, or a synthetic nucleotide sequence. In the present invention, interference fragments of a male restorer gene Ms45 and of a grain size labeling gene Mn1 are constructed into a single vector, which may restore the fertility of a male sterile mutant ms45, and meanwhile allow grains containing the transgenic sequence to be smaller, that is, labeling the grains containing the restorer gene, so as to distinguish fertile grains (a maintainer line) and sterile grains (a sterile line). In following Examples of the present invention, interference fragments of a male fertility regulating gene Ms45 and a grain size regulating gene Mn1 of a corn are constructed into a single vector, which is transformed into HiIIAxHiIIB corn hybrid, to obtain a transgenic plant, which is then back-crossed with an ms45 male sterile plant, to thereby introduce both of the interference fragments of the Ms45 restorer gene and of the Mn1 gene into a male sterile mutant ms45. Due to the presence of a wild-type Ms45 gene, the transgenic plant exhibits fertility. When the transgenic heterozygous plant (Ms45ms45ms45) is crossed with a male sterile plant (ms45ms45), two progenies will be produced, one being male sterile, normal grains free of a transgenic sequence (a sterile line, ms45ms45), which may be restored to have fertility with any of wild-type plants (Ms45Ms45), and may act as a sterile line during seed production; the other being fertile grains with smaller grains (a maintainer line, Ms45ms45ms45), which may have homozygous, recessive, male fertility regulating sites. As a result of comprising a complement transgenic sequence, the plant exhibits fertility, and in virtue of also comprising a nucleotide sequence that affects grain size, the grains become small.

Figure 7:
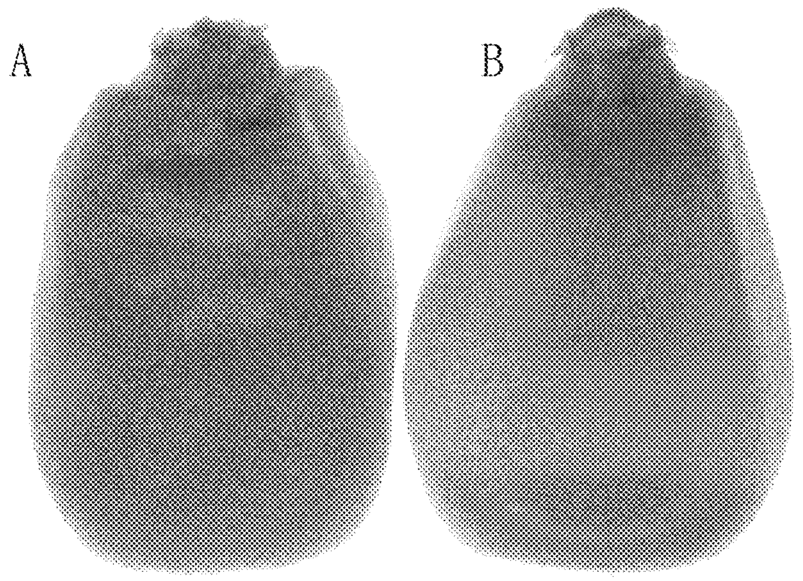
FIG. 7 shows a grain phenotype of a 16-KDγ-prolamin dominant mutant of a grain composition regulating gene.

In another embodiment of the present invention, a grain composition regulating gene, a 16-KDγ-prolamin dominant allele is used in the present invention. The 16-KDγ-prolamin gene encodes a prolamin. A mutant Mucronate (Mc), due to a deletion of 38 bases in 438-476 bp of 16-KDγ-prolamin gene which results in a variation in the encoding frame of the gene, has a translated protein significant different than a wild-type. This in turns affects the development of grain endosperm, leading to an opaque endosperm (as shown in FIG. 7, A is a Mc16-KDγ-prolamin mutant, and B is a wild-type), but have no impact on the development of embryo and plant. Since Mc is a dominant mutant, grains will exhibit opaque endosperm as long as they have the dominant allele of Mc. In the present invention, the Mc dominant allele is transformed into a wild-type through a transgenic technique, and is ensured to achieve a normal expression in the plant, and then the plant exhibits an opaque phenotype of endosperm, as indicated by A in FIG. 9. In such conditions, an individual grain having a transformed fragment existing therein a heterozygous state may be quickly distinguished through naked eyes or devices. Likewise, a similar operation may also be performed on other dominant gene(s) that affects endosperm composition development by the same method, to obtain an easily distinguishable transgenic grain. The nucleotide sequence of the 16-KDγ-prolamin gene in the present invention is derived from a Mc mutant, with a specific sequence as shown by SEQ ID No: 6, comprising a promoter sequence and a gene encoding frame sequence. The nucleotide sequence as described above is not limited to Mc mutant, and may also be derived from any other corn endosperm mutant, or a homologous gene of another species, or a synthetic nucleotide sequence. In the present invention, a vector of a 16-KDγ-prolamin gene (CheolSoo Kim et al. 2006) regulating corn endosperm composition is constructed. The vector will affect the development of endosperm, allowing for a corn having farinaceous endosperm that appears opaque. A mutant of the gene is Mucronate (Mc). The gene, if silenced, will not have an influence on other traits of the plant. During fertilization of a corn plant, a fertilized gamete comprising the vector will affect endosperm development, thereby resulting in opaque endosperm. In the present invention, a male restorer gene Ms45 and a Mc16-KDγ-prolamin endosperm labeling gene are constructed in a single vector, which may restore the fertility of a male sterile mutant ms45, while allowing for opaque endosperm of grains comprising a transgenic sequence, i.e., labeling the grains comprising a restorer gene, to distinguish fertile grains (a maintainer line) and sterile grains (a sterile line). In the present invention, a corn male fertility regulating gene Ms45 and an endosperm composition regulating Mc 16-KDγ-prolamin gene are constructed in a single vector, which is then transformed into a HiII-AxHiIIB corn hybrid plant, to obtain a transgenic plant. The transgenic plant is then backcrossed with an ms45 male sterile plant, to thereby introduce both of the Ms45 restorer gene and the Mc 16-KDγ-prolamin gene into a male sterile mutant ms45. Due to the presence of wild-type Ms45 gene, the transgenic plant exhibits fertility. When the transgenic heterozygous plant (Ms45ms45ms45) is crossed with male sterile plant (ms45ms45), two progenies will be produced, one being male sterile normal grains free of a transgenic sequence (a sterile line, ms45ms45), which may have fertility restored with any of wild-type plant (Ms45Ms45), and may act as a sterile line in seed production; the other being fertile grains with opaque endosperm (a maintainer line, Ms45ms45ms45), which may have homozygous recessive sites that regulate male fertility. As a result of inclusion of a complementary transgenic sequence, the plant exhibits fertility; and in virtue of also comprising a nucleotide sequence that affects endosperm composition, the grain endosperm is opaque.

The present invention provides an effective method for seed labeling, which is applicable not only to corn plants (*Zea mays*), but also to crops such as rice (*Oryza sativa*), *Sorghum* (*Sorghum bicolor*), wheat (*Triticumaestivum*), soybean (*Glycine max*), cotton (*Gossypiumhirsutum*), sunflower (*Helianthus annuus*), and the like.

Hereinafter, more detailed description is provided by way of explanation and illustration, which is not intended to limit the scope of the present invention.

Figure 3:
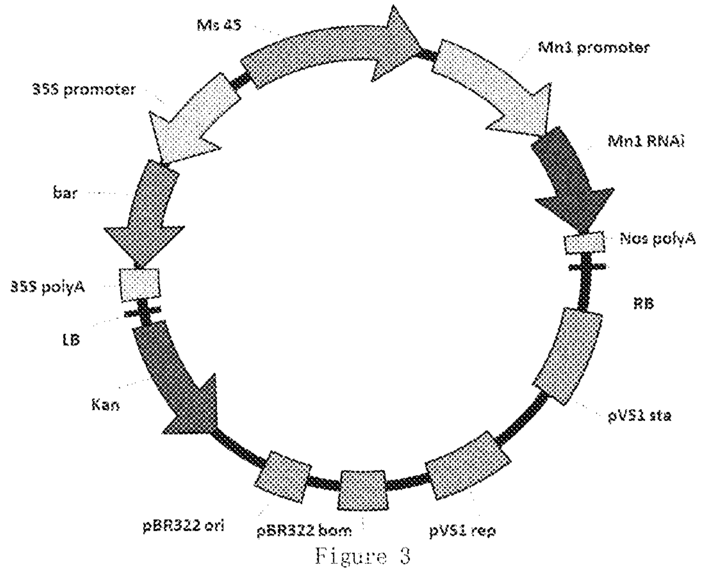
FIG. 3 shows a schematic structure diagram of a plant expression vector pMs45-Mn1RNAi comprising a male fertility gene Ms45 expression element and an expression element of an interference fragment of a grain size regulating gene Mn1.

Example 1. Construction of a Plant Transforming Vector pMs45-Mn1RNAi Comprising a DNA Fragment (a DNA Construct) that Regulates Corn Male Fertility and Corn Grain Size As shown in FIG. 3, a plant transforming vector pMs45-Mn1RNAi comprises a DNA fragment (a DNA construct) that regulates corn male fertility and corn grain size, and a selectable marker gene. Therein, the DNA fragment that regulates corn male fertility and corn grain size is designated as Ms45-Mn1RNAi that is a DNA fragment between LB and RB of pMs45-Mn1RNAi. Ms45-Mn1RNAi comprises an Ms45 expression element (a first nucleotide sequence) of SEQ ID No: 1 and an expression element (a second nucleotide sequence) for silencing Mn1 gene. The expression element for silencing Mn1 gene is formed by linking a promoter of Mn1 of SEQ ID No: 3 (a Mn1 promoter), a Mn1 interference fragment Mn1RNAi and a terminator. The Ms45 expression element is closely linked with the Mn1 gene silencing expression element, and both exist in a plant when pMs45-Mn1RNAi is transformed into the plant. A method for constructing pMs45-Mn1RNAi is as follows:

1. Amplification of Ms45 Wild-Type Allele (Ms45 Expression Element) for Restoring Male Fertility of a Corn Male Sterile Mutant Ms45

In the present invention, the ms45 male sterile mutant in Table 1 is taken as an example for particularly illustrating an embodiment. First, a wild-type allele Ms45 of ms45 was amplified, which was derived from a self-bred line B73, with a sequence as presented by SEQ ID No: 1. Taking corn self-bred line B73 genome DNA as a template, with reference to B73 genome sequence, primers were designed to amplify the whole expression element (a promoter and an encoding frame sequence of the Ms45 gene) of the gene. The amplification primers were: Ms45F: 5' tgaattcTGCTGAGTTCTCCTTGGGTTATCC 3' (SEQ ID NO:9), Ms45R: 5' tcccgggGGTTGCGCATGAAATAGGGGT 3' (SEQ ID NO:10). The upstream amplification primer had an EcoRI recognition site added at 5'-terminus, and the downstream amplification primer had a SmaI recognition site added at 5'-terminus. The amplification reaction system was of: 2 μL template DNA, 0.5 μL primer Ms45F, 0.5 μL primer Ms45R, 1.6 μL dNTP, 2 μL 10× Buffer, 0.3 μL high-fidelity taq polymerase, and 13.1 μL $ddH_2O$. The reaction conditions were: pre-denaturation at 95° C. for 5 min, denaturation at 95° C. for 45 s, anneal at 59° C. for 45 s, and extension at 72° C. for 3 min, 32 cycles, and post-extension at 72° C. for 10 min. The amplified target band had a full length of 3518 bp. After the amplification, the sequence was linked to a T-easy sequencing vector, and a positive clone was sequenced. The result of the sequencing indicated that the 3518 bp DNA comprised an Ms45 gene expression element as presented by SEQ ID No: 1, an EcoRI recognition site and a SmaI recognition site. In SEQ ID No:1, positions 8-542 represented a promoter, positions 1422-2972 represented an Ms45 gene encoding sequence, for encoding a Ms45 protein of SEQ ID No:4.

2. Preparation of Mn1 Interference Fragment Mn1RNAi for Silencing Mn1 Gene

Mn1 gene encodes a cell wall invertase protein (with an amino acid sequence of SEQ ID No: 5), and if inactivated, will affects the development of endosperm, resulting in smaller grains (as shown in FIG. 2), but having no impact on the development of embryo and plant. In the present invention, the Mn1 gene was silenced by RNAi technique, and an interference fragment used was designated as Mn1RNAi, with a structure of Mn1SEQ$_{for}$-X-Mn1SEQ$_{rev}$, wherein the Mn1SEQ$_{rev}$ has a sequence that is reversely complementary to that of Mn1SEQ$_{for}$, and X is an intron forming a hairpin structure. Mn1RNAi had a nucleotide sequence as presented by SEQ ID No:2, wherein positions 7-13 represented a BstEII recognition sequence, positions 14-276 represented the nucleotide sequence of Mn1SEQ$_{for}$, positions 277-400 represented X as an intron forming a hairpin structure, positions 401-663 represented the nucleotide sequence of Mn1SEQ$_{rev}$, and positions 664-669 represented a HindIII recognition sequence.

3. Cloning of Mn1 Gene Promoter (Mn1 Promoter)

In the present invention, a promoter (Mn1 promoter) of a grain size regulating gene Mn1 was used to promote Mn1 interference fragment Mn1RNAi, wherein Mn1 gene was specifically expressed in endosperm, such that the mRNA transcribed with the promoter existed in only endosperm cells. The promoter was derived from corn self-bred line B73 genome DNA, with a sequence particularly presented by SEQ ID No: 3. Taking corn self-bred line B73 genome DNA as a template, with reference to B73 genome sequence, primers were designed to amplify the promoter of the gene. The amplification primers were as follows: Mn1pro bF:5' atcccggGCTCGCATGAGAGAACAACCA 3' (SEQ ID NO:11), Mn1pro bR:5' gcaagcttGGGGGTGCTAT-TTGTACTGTGC 3' (SEQ ID NO:12), wherein the upstream amplification primer had a SmaI recognition site added at 5'-terminus, and the downstream amplification primer had a HindIII recognition site added at 5'-terminus. The amplification reaction system was of: 2 μL template DNA, 0.5 μL primer Mn1pro bF, 0.5 μL primer Mn1pro bR, 1.6 μL dNTP, 2 μL 10× Buffer, 0.3 μL high-fidelity taq polymerase, and 13.1 μL ddH$_2$O. The reaction conditions were: pre-denaturation at 95° C. for 5 min, denaturation at 95° C. for 45 s, anneal at 59° C. for 45 s, and extension at 72° C. for 2 min, 32 cycles, and post-extension at 72° C. for 10 min. The amplified target band had a full length of 2422 bp. After the amplification, the sequence was linked to a T-easy sequencing vector, and a positive clone was sequenced. The result of the sequencing indicated that the 2422 bp DNA was a Mn1 gene promoter fragment, and the Mn1 gene promoter fragment comprised a Mn1 gene promoter of SEQ ID No: 3, a SmaI recognition site and a HindIII recognition site.

4. Construction of pMs45-Mn1RNAi

A plant transforming vector pMs45-Mn1RNAi, as shown in FIG. 3, was constructed by assembling the DNA components in above steps 1, 2 and 3.

The plant transforming vector pMs45-Mn1RNAi, comprising a male fertility gene Ms45, a Mn1 interference fragment expression element, and a selectable marker gene bar expression element, was constructed with a plasmid pCAMBIA3301 (Center for the Application of Molecular Biology to International Agriculture (CAMBIA), Australia) as a skeleton DNA. First, the Mn1 interference fragment Mn1RNAi and pCAMBAI3301 in step 2 were digested with BstEII and HindIII. Large fragments of the Mn1 interference fragment Mn1RNAi and pCAMBAI3301 were linked, and detected for a positive clone. Then, the positive clone and the 3518 bp DNA (an Ms45 expression element) in step 1 were double digested with EcoRI and SmaI, and target bands were recovered. These two fragments were linked and detected for a positive clone. Finally, the positive clone and the Mn1 gene promoter in step 3 were digested with SmaI and HindIII, and target bands were recovered. Two fragments were linked and detected for a positive clone. A plant transforming vector pMs45-Mn1RNAi (FIG. 3) was obtained comprising the male fertility gene Ms45, the expression element of Mn1 interference fragment and the expression element of the selectable marker gene bar. pMs45-Mn1RNAi was a recombinant expression vector formed by substituting the fragment between EcoRI and SmaI recognition sites in pCAMBAI3301 with the Ms45 gene expression element as presented by SEQ ID No: 1, substituting the fragment between SmaI and HindIII recognition sites in pCAMBAI3301 with the Mn1 gene promoter as presented by SEQ ID No: 3, and substituting the fragment between BstEII and HindIII recognition sites in pCAMBAI3301 with the Mn1RNAi as presented by SEQ ID No: 2.

Example 2. Preparation of a Second Plant with Heterozygous Ms45-Mn1RNAi and Homozygous Ms45

I. Transformation of a Corn Plant with the Plant Transforming Vector pMs45-Mn1RNAi in Example 1

Figure 6:
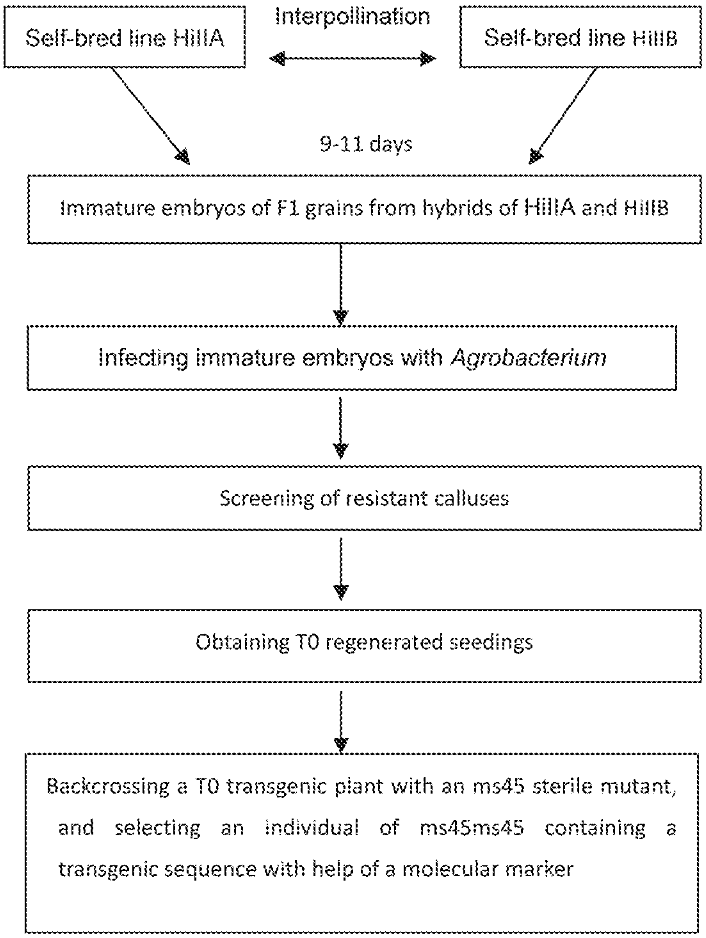
FIG. 6 shows a flow chart of a genetic transformation experiment of corn.

In the present invention, a transgenic plant was obtained by a method of infecting immature embryo of a corn with *Agrobacterium*. First, *Agrobacterium tumefaciens* EHA105 was transformed with the plant transforming vector pMs45-Mn1RNAi in Example 1, and then the *Agrobacterium* comprising the target gene was used to infect immature embryo of a corn, by a transgenic method particularly as below:

During the transgenic process in the lab, a recipient plant used was an F1 hybrid from self-bred lines HiIIA and HiIIB. The self-bred lines HiIIA and HiIIB of a corn plant (Armstrong C L, Green C E and Phillips R L. Development and availability of germplasm with high Type II culture formation response. Maize Genetics Cooperation News Letter, 1991, 65:92-93) were used. First, corn plants of self-bred lines HiIIA and HiIIB were grown in the field, and covered with bags at the time of pollination of the self-bred lines; next was pollination, in two ways: HiIIA acting as the female parent, and HiIIB acting as the male parent; HiIIA as the male parent, and HiIIB as the female parent. An immature embryo of a grain on a pollinated ear was taken days 9-11 after pollination, and infected with *Agrobacterium tumefaciens* EHA105 indoors. Immature embryo infected by *Agrobacterium tumefaciens* EHA105 was placed on a selective medium for repeated screenings, to obtain a resistant callus, which was then regenerated into a seedling, to obtain a T0 transgenic plant. Thereafter, some female parents for seed production and Ms45 male sterility materials were crossed with pollen from the T0 transgenic plant, and phenotypes were observed. A specific flow chart in the experiment is shown in FIG. 6.

With *Agrobacterium tumefaciens* EHA105 infection, pMs45-Mn1RNAi was introduced into an immature embryo of a recipient plant, and then screened with an herbicide, Bialaphos, to obtain a transgenic plant. Particularly, the method was as below:

(I) Stripping of Immature Embryo

1. Removal of bracteal leaves. About 1 cm from the tip of an ear were cut off, and from the tip a tweezer was inserted into the ear, so that the tweezer may serve as a handle to facilitate operations. Then, the ear was placed into a beaker filled with a disinfectant. 4-6 ears may be placed into the same beaker, as desired in practice.

2. To the beaker, about 700 ml of a disinfectant (50% of a bleaching agent or 5.25% of sodium hypochlorite, with one drop of Tween 20 added) was added to immerse the ears. During 20 min disinfection, the ears were sometimes were turned around while the beaker was tapped to drive out bubbles on the surface of the grains, to thereby achieve the best disinfection. After the disinfection was completed, the ears were placed into a beaker filled with sterilized water, and washed 3 times, and then were ready for embryo stripping.

3. An end of a disinfected ear was placed on a large dish, and tips (1.5-1.8 mm) of the grains were cut off with a large scalpel, during which the tools used such as blade of the scalpel, the dish, embryo stripping knife, etc. were frequently disinfected.

4. Between embryo and endosperm, an embryo stripping knife was inserted with its knifepoint, and immature embryo was carefully pried out. The immature embryo was gently jacked up with a small scalpel tip, to protect the immature embryo from any injury. The immature embryo was placed on an N6E medium, with the hypocotyl side thereof in close contact with a filter paper on the medium. The embryos were arranged in a density of about 2×2 cm (30/dish).

5. The dish was sealed with a sealer membrane, and cultured at 28° C. for 2-3 days.

(II) *Agrobacterium* Infection

1. *Agrobacterium tumefaciens* EHA105 was cultured in a YEP (containing 33 mg/L of kanamycin and 100 mg/L of rifampicin) medium a week in advance, and stored in a refrigerator at 4° C. for about one month, and should be stored with glycerol at −80° C. for long term storage.

2. *Agrobacterium tumefaciens* EHA105 was cultured on a YEP medium at 19° C. for 3 days, with an addition of kanamycin to a concentration of 33 mg/L, and of rifampicin to a concentration of 50 mg/L.

3. After 3 days, *Agrobacterium tumefaciens* EHA105 was picked and placed into 5 mL infection medium in a 50 ml centrifuge tube, with adding AS(inf+AS) (having solutes as shown in Table 2, and a solvent of water), and incubated with shaking at room temperature (25° C.) at 75 rpm for 2-4 hours.

4. Infection of immature embryo. The stripped immature embryos were immediately placed into a centrifuge tube containing a liquid medium AS (inf+AS) (2 ml), about 20-100 immature embryos per tube, and washed with such medium 2 times, and then added with 1-1.5 ml of a certain concentration (OD550=0.3-0.4) of *Agrobacterium*. After carefully inversing the centrifuge tube 20 times, the tube was placed upright in a dark box for 5 min, ensuring that all of the immature embryos were immersed in the liquid of *Agrobacterium*. Vortexing should be avoided in the whole process.

(III) Co-Culture

1. After infection, the infected immature embryos were transferred to a co-culture medium (having solutes as shown in Table 2, and a solvent of water), bringing the hypocotyls of the immature embryos in contact with the surface of the medium, while driving out excessive *Agrobacterium* on the surface of the medium.

2. The dish was sealed with a sealer membrane, and culture was performed in dark at 20° C. for 3 days.

(IV) Resting Culturing

After 3-day co-culture, the immature embryos were transferred onto a resting medium (having solutes as shown in Table 2, and a solvent of water), and the dish was sealed with a sealer membrane, for culture in dark at 28° C. for 7 days.

(V) Selection

After 7 days, all of the immature embryos were transferred onto a selective medium (having solutes as shown in Table 2, and a solvent of water) (35 immature embryos/dish), and cultured for two weeks. The selective medium contains 1.5 mg/L of Bialaphos. After two weeks, subculture was performed with a concentration of Bialaphos up to 3 mg/L.

2. With infection of about 5 weeks, cells containing a transformant would grow into observable type II calluses.

(VI) Regeneration of Transgenic Plant

1. After growth on regeneration medium I (having solutes as shown in Table 2, and a solvent of water) for 3 weeks, followed by germination on regeneration medium II (having solutes as shown in Table 2, and a solvent of water) (in a light culture room), 100 corn plants transformed with T0 pMs45-Mn1RNAi were obtained.

2. The regenerated seedlings were grown until 3-4 leaves appeared, and transferred into a greenhouse. When grown into a fusule and pollination stage, these seedlings were pollinated.

TABLE 2

| | Solutes and their contents in media | | | | | |
|---|---|---|---|---|---|---|
| Type | AS(inf + AS) | Co-culturemedium | Resting-medium | Selective-medium | Regeneration medium I | Regeneration medium II |
| Component | | | | | | |
| MS salt | 2.16 g/L | 4.33 g/L | 4.33 g/L | 4.33 g/L | 4.33 g/L | 2.16 g/L |
| Sucrose | 68.5 g/L | 30 g/L | 30 g/L | 30 g/L | 30 g/L | 30 g/L |
| Glucose | 30 g/L | | | | | |
| L-proline | 0.115 g/L | 1.38 g/L | 1.38 g/L | 1.38 g/L | 1.38 g/L | |
| Vitamin $B_1$ | | 0.5 mg/L | 0.5 mg/L | 0.5 mg/L | 0.5 mg/L | |
| 2,4-D | | 5 mg/L | 5 mg/L | 5 mg/L | | |

TABLE 2-continued

Solutes and their contents in media

| Type | AS(inf + AS) | Co-culturemedium | Resting-medium | Selective-medium | Regeneration medium I | Regeneration medium II |
|---|---|---|---|---|---|---|
| 6-BA | | 0.01 mg/L | 0.01 mg/L | 0.01 mg/L | 3.5 mg/L | |
| IBA | | | | | | 0.75 mg/L |
| NAA | | | | | | 0.5 mg/L |
| 4-amino-3,5,6-trichloropyridine-carboxylic acid (picloram) | | | | | 1 mg/L | |
| Timentin | | | 100 mg/L | 100 mg/L | 100 mg/L | |
| Bialaphos | | | | 3 mg/L | 3 mg/L | 3 mg/L |
| Agar | | 6 g/L | | | | |
| phytagel | | | 3 g/L | 3 g/L | 3 g/L | 3 g/L |
| pH | 5.7 | 5.7 | 5.7 | 5.7 | 5.7 | 5.7 |
| AgNO3 | | 3.4 mg/L | 3.4 mg/L | 3.4 mg/L | | |
| Acetosyringone | 200 μmol/L | 200 μmol/L | 200 μmol/L | | | |

In Table 2, MS salt was commercial available from phyto Technology Laboratories, LLC, Art. No. M524.

II. Changing the Ms45Ms45 Wild-Type Self-Bred Line into an ms45ms45 Homozygous Recessive Self-Bred Line An ms45 homozygous recessive mutant (*Maize Genetics Cooperation Stock Center*, 905I) as the female parent was crossed with a different self-bred line (e.g., Zheng 58) to obtain F1, which was further backcrossed with the corn self-bred line of Zheng 58 (Henan Qiule Seed Industry Science & Technology Co. Ltd., China), to obtain a BC1 population for genotype analysis. Plants identified as having a heterozygous Ms45 site was further backcrossed with Zheng 58. After 5-6 generations of backcross as such, individuals that had a heterozygous Ms45 site with the rest of the sites all from Zheng 58 were screened out using a molecular marker, and self-bred to thereby obtain an ms45 homozygous recessive self-bred line of Zheng 58 (Zheng 58 (ms45ms45)). The self-bred line may serve as a sterile line, and was called the first plant.

III. Preparation of a Second Plant Having Heterozygous Ms45-Mn1RNAi and Homozygous Ms45

The ms45 homozygous recessive self-bred line (a female parent) was crossed with the pMs45-Mn1RNAi transformed T0 corn plant (a male parent) obtained in procedure I, and subjected to multiple backcrosses with the ms45 homozygous recessive self-bred line as a recurrent parent. The pMs45-Mn1RNAi transformed T0 corn plant obtained in procedure I was changed into a self-bred line comprising Ms45-Mn1RNAi and having a homozygous recessive ms45 site and heterozygous Ms45-Mn1RNAi. This self-bred line is the second plant having heterozygous Ms45-Mn1RNAi and homozygous ms45.

For above purpose, 50 of the pMs45-Mn1RNAi transformed T0 corn plants (a male parent) obtained in procedure I were crossed with the ms45 homozygous recessive self-bred line of Zheng 58 (Zheng 58 (ms45ms45)) (a female parent) obtained in procedure II. From the hybrid progenies, those grains with a small size were selected and sowed in the field, and subsequently sprayed with 200 mM Bialaphos. Survived plants were further backcrossed with the ms45 homozygous recessive self-bred line of Zheng 58 (Zheng 58 (ms45ms45)) obtained in procedure II. After 5-6 generations of backcross as such, individuals that had a heterozygous transgenic site (Ms45-Mn1RNAi) and a homozygous recessive Ms45 site with the rest of the sites all of Zheng 58 background were screened out using a molecular marker. Such an individual is the second plant having heterozygous Ms45-Mn1RNAi and homozygous ms45, and was called the second plant of Zheng 58 (Ms45ms45ms45).

Figure 4:
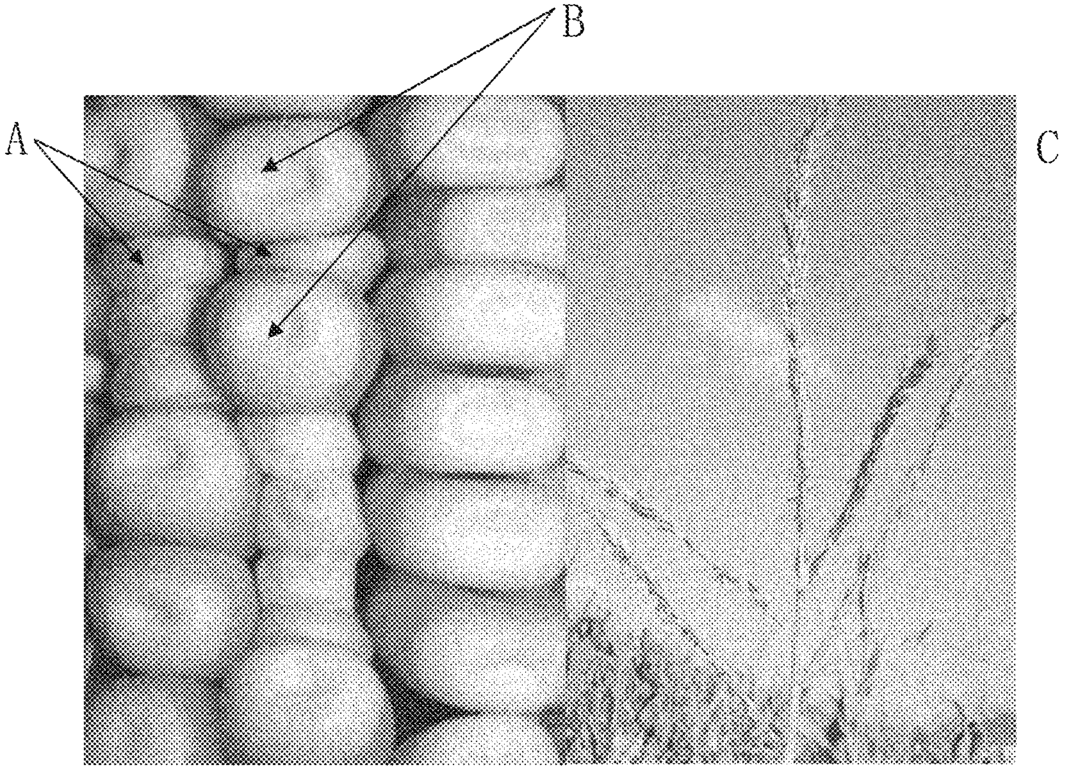
FIG. 4 shows male flower and grain phenotypes of a plant transformed with a plant expression vector having a male fertility gene Ms45 expression element and an expression element of an interference fragment of a grain size regulating gene Mn1.
Figure 5:
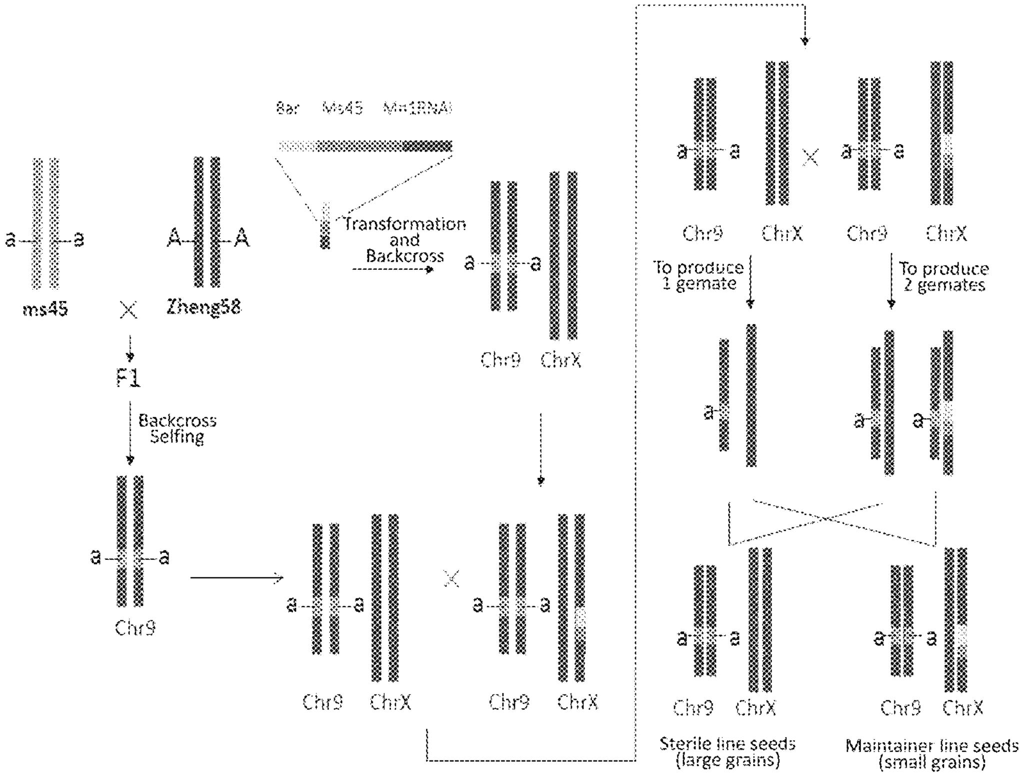
FIG. 5 shows a route chart of a seed production using a nuclear male sterility gene, a grain size regulating gene and a transgenic technique.

Above second plant of Zheng 58 (Ms45ms45ms45) as a male parent was crossed with the ms45 homozygous recessive self-bred line of Zheng 58 (Zheng 58 (ms45ms45)) (a female parent) obtained in procedure II, to produce progenies, which included not only a male sterile line of Zheng 58 (ms45ms45) with a normal grain size (as indicated by B in FIG. 4), but also a maintainer line of the male sterile Zheng 58 (ms45ms45), Zheng 58 (Ms45ms45ms45), with a smaller grain size (as indicated by A in FIG. 4). Specific process for selection and culture is shown in FIG. 5.

IV. Analysis of the pMs45-Mn1RNAi Transformed T0 Corn Plant Obtained in Procedure I The pMs45-Mn1RNAi transformed T0 corn plant and progenies thereof obtained in procedure I were assessed in terms of the overall morphology of the plant, and particularly analyzed for pollen and grain phenotypes. Except for grains, no difference in morphology was observed between a pMs45-Mn1RNAi transformed T0 corn plant and a non-transgenic control plant. When the pMs45-Mn1RNAi transformed T0 corn plant was crossed with an ms45 male sterility material, among the hybrid progenies, those plants comprising Ms45-Mn1RNAi exhibited fertility, as indicated by C in FIG. 4, while the hybrid progenies free of Ms45-Mn1RNAi exhibited complete sterility. This suggested that the performance of male sterility of the homozygous recessive ms45 was compensated by the expression of Ms45 gene, and meanwhile those grains comprising Ms45-Mn1RNAi were smaller than the normal grains free of Ms45-Mn1RNAi, and had a phenotype the same as the mn1 mutant, as indicated by A in FIG. 4. This suggested that the interference fragment of Mn1 gene could have a normal function in all transgenic plants. Moreover, the small size grains and normal grains that have been subjected to the grain phenotype identification were sowed by the inventors in the field, and all of these grains were capable of normal germination, with no significant difference in germination rate in comparison with normal grains. When the plants were grown to appear 4-5 leaves, 200 mM bialaphos was sprayed. As a result, all of the small size grains could survive as normal, with no inhibition of growth, however, all of the seedlings from the normal grains were dead. This suggested that all of the Ms45 male fertility gene and the mn1 interference fragment as well as the selectable marker gene bar could function as normal, and these three genes allowed for a linkage inheritance. In the progenies produced by the hybridization of the pMs45-Mn1RNAi transformed plant with the male sterile mutant ms45, a ratio of the normal grains: the smaller grains was 1:1.

The specific experimental method of FIG. 4 is the same as that in procedure III.

Example 3. Large-Scale Propagation of an Ms45 Male Sterile Self-Bred Line Using the Male Sterile Maintainer Line in Example 2

Taking a self-bred line of Zheng 58 as an example, the male sterile line of Zheng 58 (ms45ms45) in Example 2 and the male sterile maintainer line of Zheng 58 (Ms45ms45ms45) in Example 2 were sowed in the field alternately with 5 rows of the sterile line and 1 row of the maintainer line, in the condition of ensuring no additional corn planted around, allowing for a natural pollination between the sterile line and the maintainer line. The maintainer line would receive only its own pollen to produce progenies. Since the grains having a homozygous transgenic composition (Ms45-Mn1RNAi) were indistinguishable from heterozygous grains in the produced progenies, these grains were discarded. The normal size grains (having a large size) might serve as a sterile line. The male sterile line of Zheng 58 (ms45ms45) received the pollen from the male sterile maintainer line of Zheng 58 (Ms45ms45ms45) to produce progenies, wherein normal size grains belonged to a sterile line without a transgenic composition, and smaller size grains belonged to a maintainer line with a transgenic composition. The maintainer line all was used to propagate the sterile line and the maintainer line in the next year, and most of the sterile line was used to produce commercial seeds, and a small remaining part was used to propagate the sterile line and the maintainer line in the next year. A specific flow chart of the production is shown in FIG. 5.

Example 4. Large-Scale Production of Hybrid Seed Using the Male Sterile Line in Example 3

The sterile line produced in Example 3 is a homozygous recessive sterile line regulated by cell nucleus, and such a sterile line may have fertility restored with any wild-type plant (Ms45Ms45). Therefore, as long as a self-bred line, such as Chang 7-2, that has high combining ability with the male sterile (ms45ms45) self-bred line, e.g., male sterile Zheng 58 (ms45ms45), is selected for hybridization, hybrid seeds having excellent agronomic traits may be produced. For this purpose, the inventors sowed the male sterile self-bred line and the wild-type self-bred line alternately in the field, with ensuring no additional corn planted around within 300 meters, so that the ears of the sterile line would receive only the pollen from the wild-type self-bred line, while the wild-type self-bred line was only capable of selfing. Thus, the seeds produced on the ears of the sterile line were hybrid seeds.

Example 5. Construction of a Plant Transforming Vector pMs45-Mc 16-KDγ-Zein Comprising a DNA Fragment (a DNA Construct) that Regulates Corn Male Fertility and Corn Grain Endosperm Composition The plant transforming vector pMs45-Mc 16-KDγ-zein, as show in FIG. 8, comprised a DNA fragment (a DNA construct) that regulated corn male fertility and corn grain endosperm transparency and a selectable marker gene. Therein, a DNA fragment that regulated corn male fertility and corn grain size was designated as Ms45-Mc 16-KDγ-zein, i.e., a DNA fragment between LB and RB in pMs45-Mc 16-KDγ-zein. Ms45-Mc 16-KDγ-zein comprised an Ms45 expression element (a first nucleotide sequence) of SEQ ID No: 1 and an Mc16-KDγ-prolamin gene expression element (a second nucleotide sequence) of SEQ ID No: 6. The Ms45 expression element was closely linked to the Mc16-KDγ-prolamin gene expression element, and when the pMs45-Mc 16-KDγ-zein was transformed into a plant, these two expression elements coexisted in the plant. The pMs45-Mc 16-KDγ-zein was constructed by a method as below:

1. Amplification of an Ms45 Wild-Type Allele (the Ms45 Expression Element) Restoring the Male Fertility of Corn Male Sterile Mutant Ms45

The step is same as step 1 in Example 1.

2. Artificial Synthesis of Mc Mutant 16-KDγ-Prolamin Gene

According to the report of the mutant in CheolSoo Kim et al. 2006 and the instruction of the sequence (Gene accession no. DQ826676), the gene was synthesized into an Mc16-KDγ-prolamin gene expression element as presented by SEQ ID No:6, with a HindIII restriction site added at 5'-terminus and a BstEII restriction site added at 3'-terminus. In SEQ ID No:6, positions 9-1149 represented a promoter sequence, positions 1244-1780 represented encoding sequence of Mc16-KDγ-prolamin gene, encoding Mc16-KDγ-prolamin of SEQ ID No:7.

Figure 8:
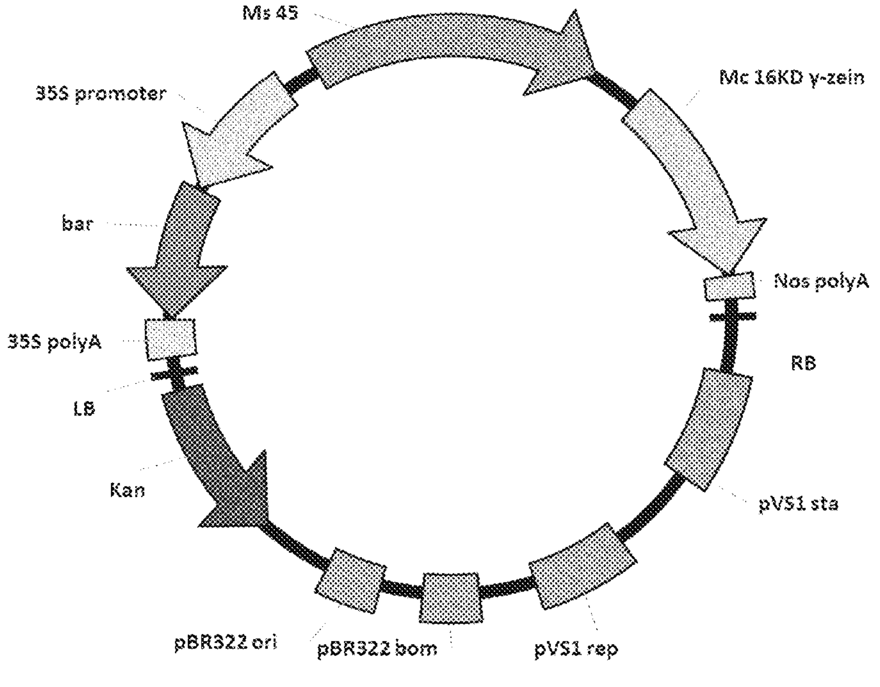
FIG. 8 shows a schematic structure diagram of a plant expression vector pMs45-Mc 16-KDγ-zein comprising a male fertility gene Ms45 expression element and an expression element of a grain composition regulating gene, 16-KDγ-prolamin dominant allele.

3. Construction of a Plant Transforming Vector pMs45-Mc 16-KDγ-Zein Comprising a Male Fertility Gene Ms45 and a Mc Mutant 16-KDγ-Prolamin Gene Expression Element as Well as a Selectable Marker Gene With a plasmid pCAMBAI3301 as a skeleton DNA, a plant transforming vector pMs45-Mc 16-KDγ-zein comprising a male fertility gene Ms45 and a Mc16-KDγ-prolamin expression element as well as a selectable marker gene bar was constructed. First, the Mc16-KDγ-prolamin expression element and pCAMBIA3301 (Center for the Application of Molecular Biology to International Agriculture (CAMBIA), Australia) were digested with BstEII and HindIII, and large fragments of the Mc16-KDγ-prolamin expression element and pCAMBAI3301 were linked, and detected for a positive clone. Thereafter, the positive clone and the Ms45 wild-type allele in step 1 were double digested with EcoRI and SmaI, and target bands were recovered. These two fragments were linked, and detected for a positive clone, to obtain a plant transforming vector pMs45-Mc 16-KDγ-zein comprising the male fertility gene Ms45 and the Mc 16-KDγ-prolamin expression element as well as the selectable marker gene bar (the constructed vector is shown in FIG. 8). pMs45-Mc 16-KDγ-zein was a recombinant expression vector in which the fragment between EcoRI and SmaI recognition sites of pCAMBAI3301 was substituted with the Ms45 gene expression element as presented by SEQ ID No: 1, and the fragment between BstEII and HindIII recognition sites of pCAMBAI3301 was substituted with the Mc16-KDγ-prolamin gene expression element as presented by SEQ ID No: 6.

Example 6. Preparation of the Second Plant Having Heterozygous Ms45-Mc 16-KDγ-Zein and Homozygous Ms45

I. Transformation of a Corn with the Plant Transforming Vector pMs45-Mc 16-KDγ-Zein in Example 5

In the present invention, a transgenic plant was obtained by a method of infecting immature embryo of a corn with *Agrobacterium*. First, *Agrobacterium tumefaciens* EHA105 was transformed with the plant transforming vector pMs45-Mc 16-KDγ-zein in Example 5, and then the *Agrobacterium* comprising the target gene was used to infect the immature embryo of an F1 hybrid corn of self-bred lines HiIIA and HiIIB. The *Agrobacterium* infected immature embryo was placed on a selective medium for repeated screenings, to obtain a resistant callus, which was then regenerated into a seedling, to obtain a T0 transgenic plant. Thereafter, pollen from the T0 transgenic plant were used to cross to some female parents and Ms45 male sterility materials in seed production, and phenotypes were observed. Specific experimental method is the same as procedure I in Example 2.

II. Changing the Ms45Ms45 Wild-Type Self-Bred Line into an ms45ms45 Homozygous Recessive Self-Bred Line An ms45 homozygous recessive mutant (*Maize Genetics Cooperation Stock Center*, 905I) as the female parent was crossed with a corn self-bred line of Zheng 58 (Henan Qiule Seed Industry Science & Technology Co. Ltd.) to obtain F1, which was further backcrossed with the corn self-bred line of Zheng 58 (Henan Qiule Seed Industry Science & Technology Co. Ltd., China), to obtain a BC1 population for genotype analysis. Plants identified as having a heterozygous Ms45 site was further backcrossed with Zheng 58. After 5-6 generations of backcross as such, individuals that had a heterozygous Ms45 site with the rest of the sites all from Zheng 58 were screened out by using a molecular marker, and self-bred to thereby obtain an ms45 homozygous recessive self-bred line of Zheng 58 (Zheng 58 (ms45ms45)). The self-bred line may serve as a sterile line, and was called the first plant. Specific experimental method is the same as procedure II in Example 2.

III. The Second Plant Having Heterozygous Ms45-Mc 16-KDγ-Zein and Homozygous Ms45

The ms45 homozygous recessive self-bred line (a female parent) was crossed with the pMs45-Mc 16-KDγ-zein transformed T0 corn plant (a male parent) obtained in procedure I, and subjected to multiple backcrosses with the ms45 homozygous recessive self-bred line as a recurrent parent. The pMs45-Mc 16-KDγ-zein transformed T0 corn plant obtained in procedure I was changed into a self-bred line comprising Ms45-Mc 16-KDγ-zein and having a homozygous recessive ms45 site and heterozygous Ms45-Mc 16-KDγ-zein. This self-bred line is the second plant having heterozygous Ms45-Mc 16-KDγ-zein and homozygous ms45.

For achieving above purpose, 50 of the pMs45-Mc 16-KDγ-zein transformed T0 corn plants (a male parent) obtained in procedure I were crossed with the ms45 homozygous recessive self-bred line of Zheng 58 (Zheng 58 (ms45ms45)) (a female parent) obtained in procedure II. From the hybrid progenies, those grains with an opaque endosperm were selected and sowed in the field, and subsequently sprayed with 200 mM Bialaphos. Survived plants were further backcrossed with the ms45 homozygous recessive self-bred line of Zheng58 (Zheng 58 (ms45ms45)) obtained in procedure II. After 5-6 generations of backcross as such, individuals that had a heterozygous transgenic site (Ms45-Mc 16-KDγ-zein) and a homozygous recessive Ms45 site with the rest of the sites all of Zheng 58 background were screened out by using a molecular marker. Such an individual is the second plant having heterozygous Ms45-Mc 16-KDγ-zein and homozygous ms45, and was called the second plant of Zheng 58 (Ms45ms45ms45).

Figure 9:
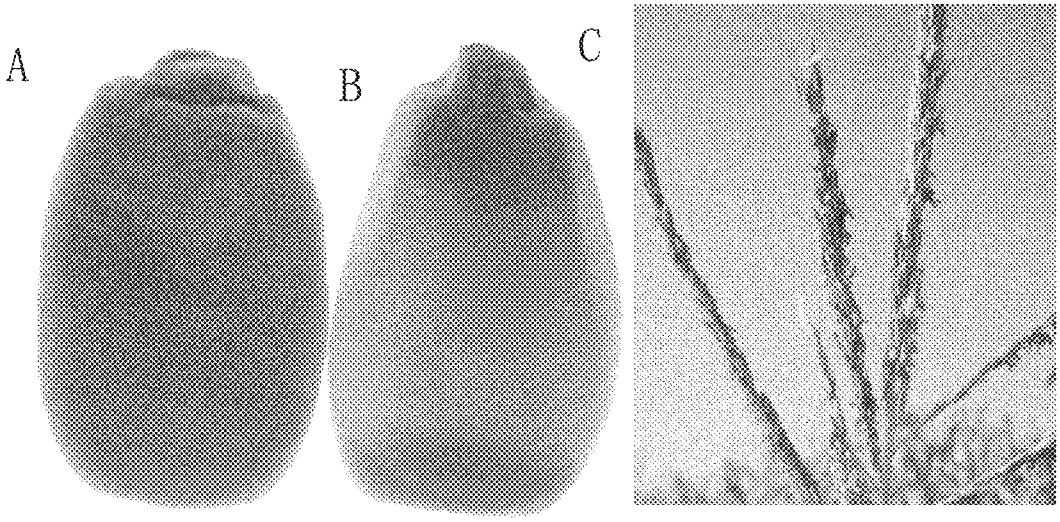
FIG. 9 shows male flower and grain phenotypes of a plant transformed with a vector having a male fertility gene Ms45 expression element and a grain composition regulating gene, 16-KDγ-prolamin dominant allele.
Figure 10:
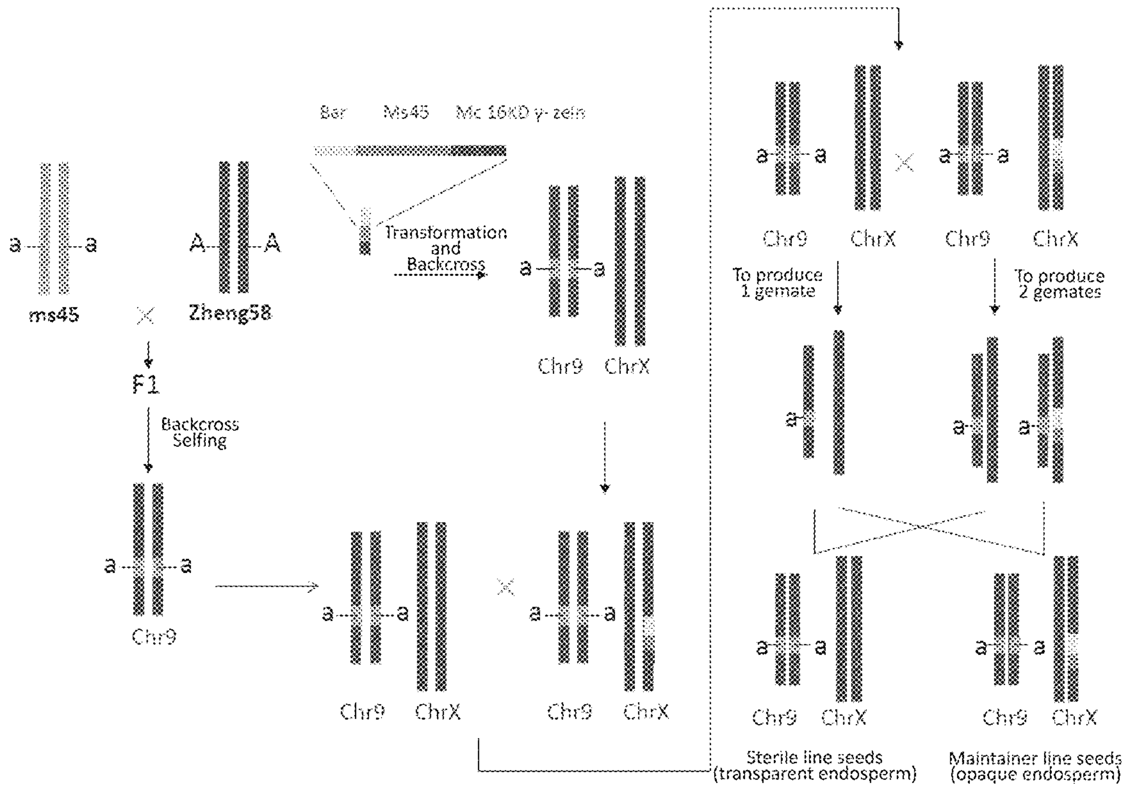
FIG. 10 shows a route chart of a seed production using a nuclear male sterility gene, an endosperm composition regulating gene, and a transgenic technique.

Above second plant of Zheng 58 (Ms45ms45ms45) as a male parent was crossed with the ms45 homozygous recessive self-bred line of Zheng 58 (Zheng 58 (ms45ms45)) (a female parent) obtained in procedure II, to produce progenies, which included not only a male sterile line of Zheng 58 (ms45ms45) with normal grains and transparent endosperm (as indicated by B in FIG. 9), but also a maintainer line of the male sterile Zheng 58 (ms45ms45), Zheng 58 (Ms45ms45ms45), with opaque endosperm (as indicated by A in FIG. 9). Specific process for selection and culture is shown in FIG. 10.

IV. Analysis of the pMs45-Mc 16-KDγ-Zein Transformed T0 Corn Plant Obtained in Procedure I The pMs45-Mc 16-KDγ-zein transformed T0 corn plant and progenies thereof obtained in procedure I were assessed in terms of the overall morphology of the plant, and particularly analyzed for pollen and grain phenotypes. Except for grains, no difference in morphology was observed between a pMs45-Mc 16-KDγ-zein transformed T0 corn plant and a non-transgenic control plant. When the pMs45-Mc 16-KDγ-zein transformed T0 corn plant was crossed with an ms45 male sterility material, among the hybrid progenies, those plants comprising a transgenic composition exhibited fertility, as indicated by C in FIG. 9, while the non-transgenic plants exhibited complete sterility. This suggested that the performance of male sterility of the homozygous recessive ms45 was compensated by the expression of Ms45 gene, and meanwhile those grains comprising the Mc mutant 16-KDγ-prolamin gene showed opaque endosperm, with a phenotype the same as the Mc mutant, as indicated by A in FIG. 9. This suggested that the Mc dominant mutant allele could have a normal function in all transgenic plants. Moreover, the opaque-endosperm grains and normal grains that have been subjected to the grain phenotype identification were sowed by the inventors in the field, and all of these grains were capable of normal germination, with no significant difference in germination rate in comparison with normal grains. When the plants were grown to appear 4-5 leaves, 200 mM Bialaphos was sprayed. As a result, all of the opaque-endosperm grains could survive as normal, with no inhibition of growth, however, all of the seedlings from the normal grains were dead. This suggested that all of the selectable marker gene bar, Ms45 male fertility gene, and Mc 16-KDγ-prolamin gene could function as normal, and these three genes allowed for a linkage inheritance. In the progenies produced by the hybridization of the transgenic plant with the male sterile mutant ms45, a ratio of the normal grains: the opaque-endosperm grains was 1:1.

The specific experimental method of FIG. 9 is the same as that in procedure III.

Example 7. Large-Scale Propagation of an Ms45 Male Sterile Self-Bred Line Using the Male Sterile Maintainer Line in Example 6

Taking a self-bred line of Zheng 58 as an example, the male sterile line of Zheng 58 (ms45ms45) in Example 6 and the male sterile maintainer line of Zheng 58 (Ms45ms45ms45) in Example 6 were sowed in the field alternately with 5 rows of the sterile line and 1 row of the maintainer line, in the condition of ensuring no additional corn planted around within 300 meters, allowing for a natural pollination between the sterile line and the maintainer line. The maintainer line would receive only its own pollen to produce progenies. Since the grains having a homozygous transgenic composition were indistinguishable from heterozygous grains in the produced progenies, these grains were discarded. The normal grains might serve as a sterile line. The sterile line material received the pollen from the maintainer line to produce progenies, wherein normal grains belonged to a sterile line without a transgenic composition, and opaque-endosperm grains belonged to a maintainer line with a transgenic composition. The maintainer line all was used to propagate the sterile line and the maintainer line in the next year, and most of the sterile lines were used to produce commercial article seeds, and a small remaining part was used to propagate the sterile line and the maintainer line in the next year. Specific flow chart of the production is shown in FIG. 10.

Example 8. Large-Scale Production of Hybrids Using the Male Sterile Line in Example 7

The sterile line produced in Example 7 is a homozygous recessive sterile line regulated by cell nucleus, and such a sterile line may have fertility restored with any wild-type plant (Ms45Ms45). Therefore, as long as a self-bred line, such as Chang 7-2, that has high combining ability with the male sterile (ms45ms45) self-bred line, e.g., male sterile Zheng 58 (ms45ms45), is selected for hybridization, hybrid seeds having excellent agronomic traits may be produced. For this purpose, the inventors sowed the male sterile self-bred line and the wild-type self-bred line alternately in the field, with ensuring no additional corn planted around within 300 meters, so that the ears of the sterile line would only receive the pollen from the wild-type self-bred line, while the wild-type self-bred line was only capable of selfing. Thus, the seeds produced on the ears of the sterile line were hybrid seeds.

INDUSTRIAL APPLICATION

In the method for propagating a sterile male plant line of the present invention, an highly effective method for seed labeling is used so that a male sterile seed of a plant may be propagated, saving manpower, reducing costs and ensuring seed purity for hybrid seed production. In the method for propagating a sterile male plant line of the present invention, a nucleotide that enables differentiation of grain shape (e.g., size, length, width, thickness, etc.) or of main endosperm nutrient material composition (e.g., starch content, oil content, presence or absence of farinaceous endosperm, etc.), a wild-type allele of a cell nuclear male sterility gene, and a transgenic technique are used to allow distinguishing fertile grains and sterile grains among the transgenic grains via grain shape (e.g., size, length, width, thickness, etc.) or endosperm nutrient material composition (e.g., starch content, oil content, presence or absence of farinaceous endosperm, etc.). The homozygous recessive male sterile plant produced by the method of the present invention may be used for producing a hybrid.

What is claimed is:

1. A method for maintaining a maize male sterile plant in a homozygous recessive state, the method comprising:
 providing a first maize plant that comprises homozygous recessive ms45 male sterility alleles;
 providing a second maize plant comprising homozygous recessive ms45 male sterility alleles that are the same as in the first maize plant, and a nucleotide construct, wherein the construct exists in a heterozygous state, and wherein the construct comprises:
 i. a first nucleotide sequence comprising a wild type allele of a male fertility regulatory gene Ms45 which results in expression of protein Ms45 having SEQ ID No: 4, in the progenies of the first plant; and
 ii. a second nucleotide sequence comprising a nucleotide sequence that inhibits the expression of the protein represented by SEQ ID No: 5, wherein the nucleotide sequence that inhibits the expression of the protein represented by SEQ ID No: 5 comprises SEQfor-X-SEC)$_{rev}$,wherein the SEQ$_{for}$ comprises a nucleotide sequence of positions 14-276 of SEQ ID No:2; the SEQ$_{rev}$ comprises the nucleotide sequence of positions 401-663 of SEQ ID No:2; the X is an intron forming a hairpin structure and comprises the nucleotide sequence of positions 277-400 of SEQ ID No:2; and
 fertilizing female gametes of the first plant with male gametes of the second plant to produce progenies maintaining the homozygous recessive state of the first plant.

2. The method according to claim 1, wherein the method is used to propagate a sterile male plant line; wherein the second nucleotide sequence in the second plant in a heterozygous state affects grain shape of the second plant, wherein the grain shape comprises size, length, width and/or thickness.

3. The method according to claim 1, wherein the first nucleotide sequence comprises an Ms45 encoding sequence having SEQ ID No: 8.

4. The method according to claim 1, wherein the first nucleotide sequence comprises the nucleotide sequence having SEQ ID No: 1.

5. The method according to claim 1, wherein the second nucleotide sequence in the second plant in a heterozygous state affects the grain size of the second plant.

* * * * *

UNITED STATES PATENT AND TRADEMARK OFFICE

CERTIFICATE OF CORRECTION

PATENT NO. : 11,572,573 B2
APPLICATION NO. : 16/370628
DATED : February 7, 2023
INVENTOR(S) : Jinsheng Lai It is certified that error appears in the above-identified patent and that said Letters Patent is hereby corrected as shown below:

On the Title Page

Column 1 (item (73) Assignee), Line 1, delete "Bejing"" and insert -- Beijing --.

In the Drawings

Sheet 3 of 7 (Figure 5), Line 6 (approx.), delete "gemate" and insert -- gamete --.

Sheet 3 of 7 (Figure 5), Line 6 (approx.), delete "gemates" and insert -- gametes --.

Sheet 4 of 7 (Figure 6), Line 6 (approx.), delete "seedings" and insert -- seedlings --.

Sheet 7 of 7 (Figure 10), Line 6 (approx.), delete "gemate" and insert -- gamete --.

Sheet 7 of 7 (Figure 10), Line 6 (approx.), delete "gemates" and insert -- gametes --.

In the Specification

Column 1, Line 36, delete "production" and insert -- production. --.

Column 1, Line 57, delete "gei-tonogany" and insert -- geitonogamy --.

Column 1, Line 58, delete "followers" and insert -- flowers --.

Column 1, Line 60, delete "followers" and insert -- flowers --.

Column 5-6 (Table 1-continued), Line 54, delete "Zeamays." and insert -- Zea mays. --.

Column 5-6 (Table 1-continued), Line 56, delete "Zeamays." and insert -- Zea mays. --.

Signed and Sealed this
Twelfth Day of September, 2023

Katherine Kelly Vidal

Katherine Kelly Vidal
*Director of the United States Patent and Trademark Office*

Column 5-6 (Table 1-continued), Line 58, delete "Zeamays." and insert -- Zea mays. --.

Column 5-6 (Table 1-continued), Line 64, delete "MaizeGenet." and insert -- Maize Genet. --.

Column 5-6 (Table 1-continued), Line 66, delete "male-sterilemutant" and insert -- male-sterile mutant --.

Column 5-6 (Table 1-continued), Line 69, delete "BEDINTGER," and insert -- BEDINGER, --.

Column 5-6 (Table 1-continued), Line 70, delete "themscal" and insert -- the msca1 --.

Column 7-8 (Table 1-continued), Line 10, delete "newmale" and insert -- new male --.

Column 7-8 (Table 1-continued), Line 14, delete "newmale" and insert -- new male --.

Column 7-8 (Table 1-continued), Line 38, delete "mutantms33" and insert -- mutant ms33 --.

Column 7-8 (Table 1-continued), Line 50, delete "1999 ." and insert -- 1999. --.

Column 12, Line 18, delete "HiIIAxHiIIB" and insert -- HiIIA×HiIIB --.

Column 12, Line 48-49, delete "HiIIAxHiIIB" and insert -- HiIIA×HiIIB --.

Column 14, Line 57, delete "HiIIAxHiIIB" and insert -- HiIIA×HiIIB --.

Column 15, Line 60-61, delete "HiIIAxHiIIB" and insert -- HiIIA×HiIIB --.

Column 16, Line 16, delete "(Triticumaestivum)," and insert -- (Triticum aestivum), --.

Column 16, Line 17, delete "(Gossypiumhirsutum)," and insert -- (Gossypium hirsutum), --.

Column 21-22 (Table 2-continued), Line 16, delete "AgNO3" and insert -- $AgNO_3$ --.

Column 25, Line 55, delete "Zheng58" and insert -- Zheng 58 --.

In the Claims

Column 45, Line 21 (approx.), Claim 1, delete "SEQfor-X-SEC)$_{rev}$, wherein" and insert -- $SEQ_{for}$-X-$SEQ_{rev}$, wherein --.